(12) United States Patent
Frankel

(10) Patent No.: US 10,345,565 B2
(45) Date of Patent: Jul. 9, 2019

(54) DEPTH AND SPEED ENHANCED ORTHOGONAL BEAM STIMULATED FLUORESCENT AND STIMULATED RAMAN EMISSION FOR IN-VIVO IMAGING

(71) Applicant: Robert David Frankel, Rochester, NY (US)

(72) Inventor: Robert David Frankel, Rochester, NY (US)

( * ) Notice: Subject to any disclaimer, the term of this patent is extended or adjusted under 35 U.S.C. 154(b) by 104 days.

(21) Appl. No.: 15/466,172

(22) Filed: Mar. 22, 2017

(65) Prior Publication Data

US 2017/0276919 A1 Sep. 28, 2017

Related U.S. Application Data

(60) Provisional application No. 62/311,565, filed on Mar. 22, 2016, provisional application No. 62/347,300, filed on Jun. 8, 2016.

(51) Int. Cl.
| | |
|---|---|
| *G02B 21/00* | (2006.01) |
| *G02B 21/06* | (2006.01) |
| *G02B 21/18* | (2006.01) |
| *G02F 1/11* | (2006.01) |
| *G02B 21/16* | (2006.01) |
| *G01N 21/64* | (2006.01) |

(52) U.S. Cl.
CPC ..... *G02B 21/0048* (2013.01); *G01N 21/6402* (2013.01); *G02B 21/0056* (2013.01); *G02B 21/06* (2013.01); *G02B 21/16* (2013.01); *G02B 21/18* (2013.01); *G02F 1/11* (2013.01)

(58) Field of Classification Search
None
See application file for complete search history.

(56) References Cited

U.S. PATENT DOCUMENTS

| | | | |
|---|---|---|---|
| 5,046,832 A | 9/1991 | Bell | |
| 5,731,588 A | 3/1998 | Hell et al. | |
| 6,351,581 B1 | 2/2002 | Doerr et al. | |
| 9,897,536 B2 | 2/2018 | Silien et al. | |
| 2001/0045529 A1* | 11/2001 | Iketaki | ........... G01J 3/4406 250/493.1 |
| 2003/0179344 A1 | 9/2003 | Van de Velde | |
| 2008/0154128 A1* | 6/2008 | Milner | ........... A61B 5/0066 600/427 |

(Continued)

OTHER PUBLICATIONS

Frankel, Robert D. (Jun. 7, 2016) "Discussion of Methods for Depth Enhancement in Single and Multiphoton-Stimulated Emission Microscopy", Journal of the Optical Society of America, vol. 33, No. 7, pp. 1421-1438.

*Primary Examiner* — Jennifer D. Carruth
(74) *Attorney, Agent, or Firm* — Tarter Krinsky & Drogin LLP

(57) ABSTRACT

A microscopy system that includes a first laser emitting a first laser pulse along a first beam line, the first laser pulse being converted into an annular Bessel pump beam; and a second laser emitting a second laser pulse along a second beam line, the second laser pulse being a probe beam, the annular Bessel pump beam and the probe beam being delivered to a sample at right angles to each other allowing the annular Bessel pump beam to shrink a focal axial diameter of the second beam line thereby enabling dipole-like backscatter stimulated emission along the second beam line.

20 Claims, 13 Drawing Sheets

(56) References Cited

U.S. PATENT DOCUMENTS

| | | |
|---|---|---|
| 2009/0279086 A1 | 11/2009 | Hell |
| 2010/0238438 A1 | 9/2010 | Frankel |
| 2010/0238498 A1 | 9/2010 | Okada et al. |
| 2011/0128538 A1 | 6/2011 | Cerullo et al. |
| 2012/0309045 A1 | 12/2012 | Knutson et al. |
| 2013/0202006 A1 | 8/2013 | Rudolph et al. |
| 2014/0285873 A1 | 9/2014 | Kieu et al. |
| 2014/0307249 A1 | 10/2014 | Peremans et al. |
| 2014/0313310 A1 | 10/2014 | Jalali et al. |
| 2014/0321772 A1 | 10/2014 | Piche et al. |
| 2015/0110150 A1 | 4/2015 | Schmidt |
| 2016/0103307 A1 | 4/2016 | Frankel |
| 2017/0219489 A1 | 8/2017 | Cheshnovsky et al. |
| 2017/0278694 A1 | 9/2017 | Chuang et al. |

\* cited by examiner

FIGURE 1A
FIGURE 1B
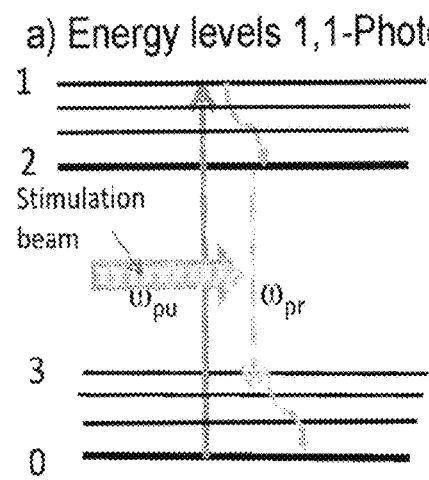
a) Energy levels 1,1-Photon
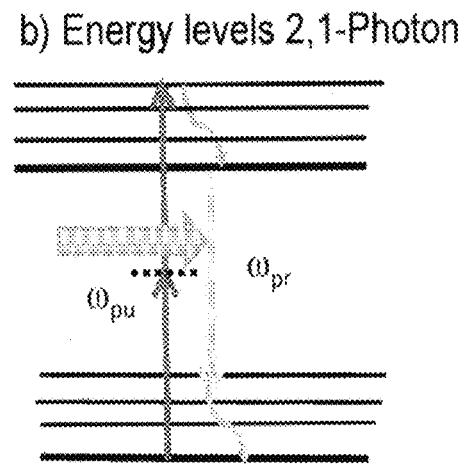
b) Energy levels 2,1-Photon
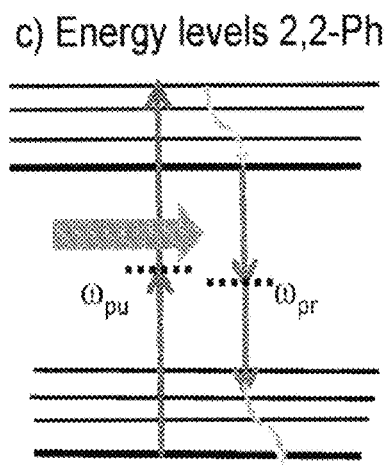
c) Energy levels 2,2-Photon
FIGURE 1C
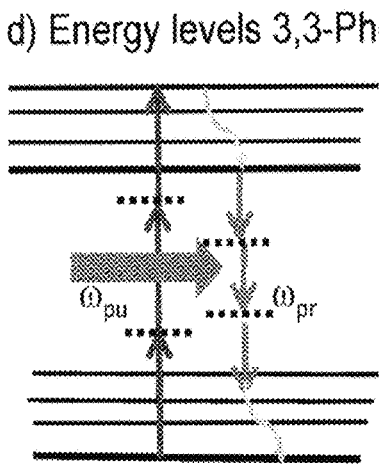
d) Energy levels 3,3-Photon
FIGURE 1D

| Molecule | 1 Photon | | 2 Photon | | 3 Photon | | 4 Photon | |
| | Pump | Probe | Pump | Probe | Pump | Probe | Pump | Probe |
| --- | --- | --- | --- | --- | --- | --- | --- | --- |
| DNA | 260nm | 320nm | 520nm | 640nm | 780nm | 960nm | 1040nm | 1240nm |
| Protein | 280nm | 340mn | 540 nm | 680nm | 840nm | 1020nm | 1120nm | 1360nm |
| NADH | 340nm | 455 nm | 680nm | 910nm | 1020nm | 1365nm | 1360nm | 1820nm |
| FAD | 450 nm | 520 nm | 900nm | 1040mn | 1350nm | 1560nm | 1800nm | 2080nm |

FIGURE 5

Bessel beam illumination

FIGURE 6A      FIGURE 6B      FIGURE 6C

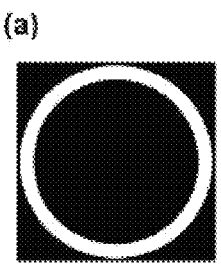 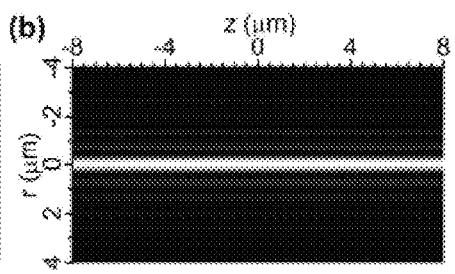 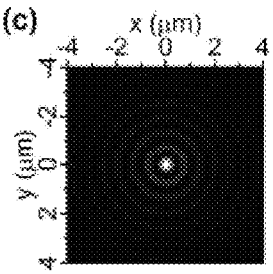

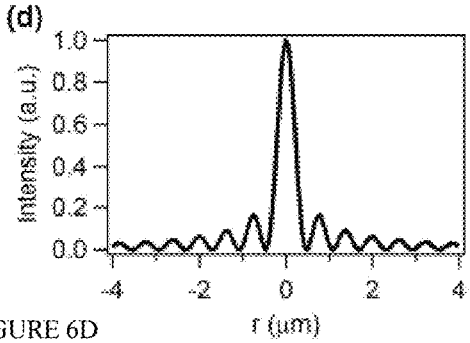 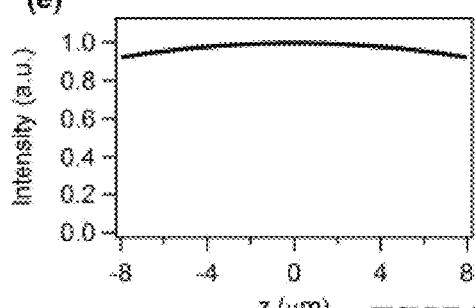

FIGURE 6D                           FIGURE 6E

Fig. 2. Creation of a zero-order Bessel beam for excitation. (a) The annular mask with a ring transmission for creating a zero-order Bessel beam; (b) Calculated intensity distribution in the r-z plane. (c) Calculated intensity distribution in the x-y plane with z = 0. (d) Lateral intensity profile of the Bessel beam. (e) Axial intensity profile of the Bessel beam. Calculations are made for an annular mask with $NA_{Bessel}^{Max} = 0.53$ and $NA_{Bessel}^{Min} = 0.50$.

Structured Illumination
a) Pump beam Bessel structured illumination
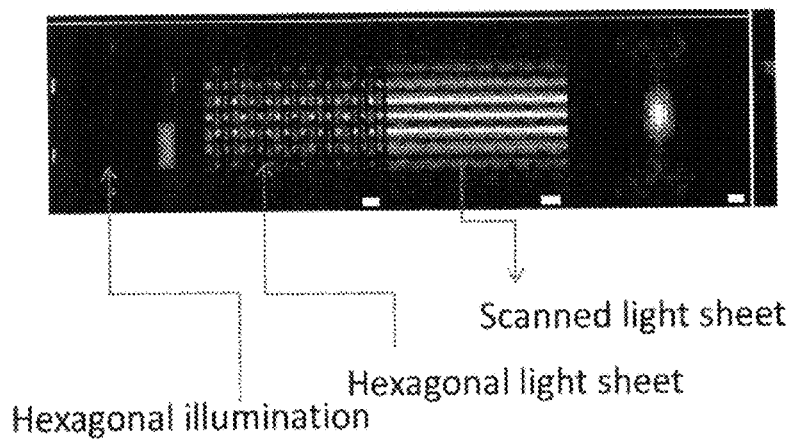
FIGURE 11A
Scanned light sheet
Hexagonal light sheet
Hexagonal illumination
FIGURE 11B
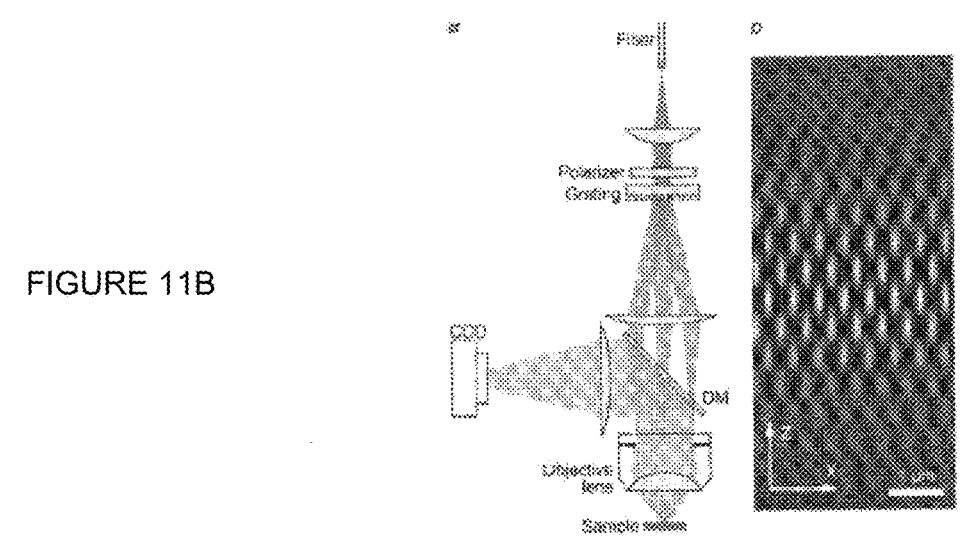

Stimulated Raman Energetics
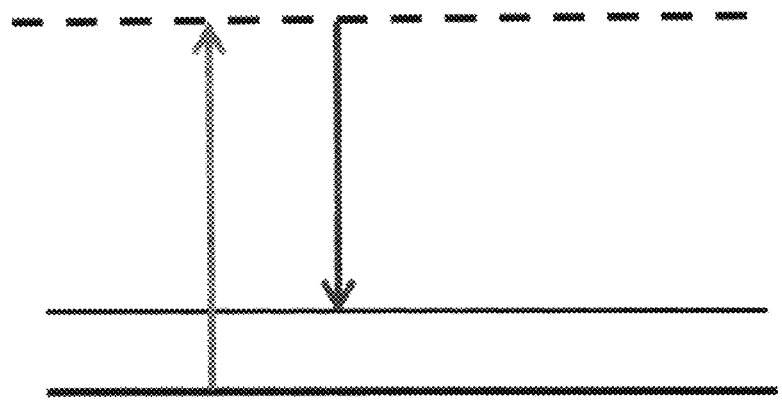
FIGIRE 12

Stimulated Raman and single photon 2• •annular aperture
FIGURE 13A          FIGURE 13B
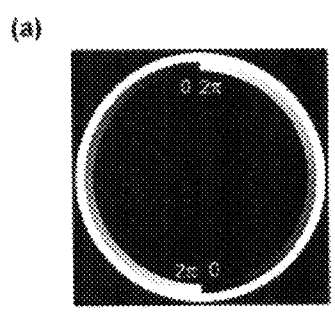
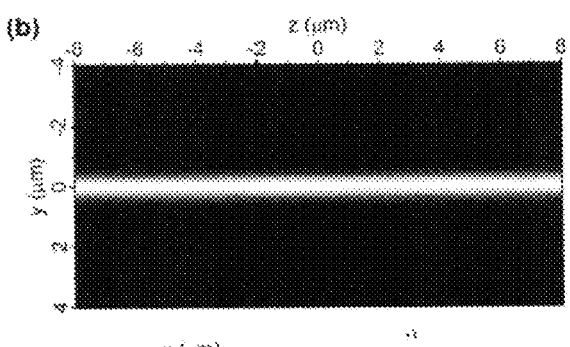
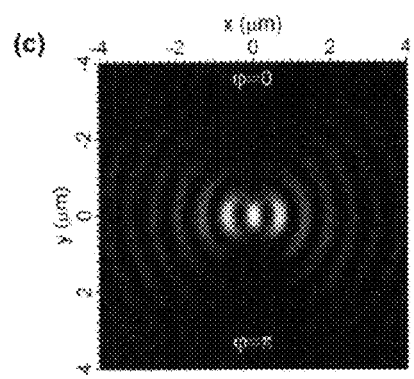
FIGURE 13C

DEPTH AND SPEED ENHANCED ORTHOGONAL BEAM STIMULATED FLUORESCENT AND STIMULATED RAMAN EMISSION FOR IN-VIVO IMAGING

CLAIM OF PRIORITY

This application claims the benefit of U.S. Provisional Application No. 62/311,565, filed on Mar. 22, 2016 and U.S. Provisional Application No. 62/347,300, filed on Jun. 8, 2016, both of which are hereby incorporated by reference in their entireties.

CO-PENDING APPLICATION

The following co-pending patent application, U.S. patent application Ser. No. 15/466,206, filed on Mar. 22, 2017, now U.S. Pat. No. 10,054,778, issued Aug. 21, 2018, entitled "Orthogonal Confocal Stimulated Emission Microscopy" is being filed concurrently herewith and is hereby incorporated by reference in its entirety.

BACKGROUND

This disclosed technology relates to stimulated emission fluorescence and stimulated Raman microscopy and more particularly to in-vivo stimulated emission.

There is interest in providing deep imaging for use in research, neuroscience, endoscopy, dermatology and intra-surgical definition of clear margins during removal of malignant tissues. For example, Optical Coherence Tomography (OCT) can obtain images up to 1 mm depth in tissue.

Multi-Photon Excitation (MPE) imaging can enhance the depth of penetration by using infrared photons for excitation where tissue absorption is low. MPE uses two or more photons to excite emission as shown in FIG. 1b. In MPE, the two or more photons can be simultaneously absorbed by one molecule, through the population of one, or more, very short lived virtual states.

MPE excitation has also been used in Fluorescence Lifetime Microscopy (FLIM), for example, to measure the fluorescent lifetimes of bound and free state metabolic cofactor NADH. Fluorescent lifetimes are of importance when determining a metabolic state of cells, in accessing tissue health and differentiating normal from malignant cells. MPE, however, is relatively slow because the fluorescent yield of free NADH is low, has a short excited state lifetime and needs photon counting to create a decay curve.

Standard fluorescence is an incoherent spontaneous emission process where emission of one or multiple photons causes fluorescent emission. In standard fluorescence, the incoherent spontaneous emission can be red shifted from the excitation and can be considered a dark field imaging technique. The measurement process for standard fluorescence is limited to background fluorescence and electrical noise.

Stimulated fluorescent emission (STEM) imaging is a combination of incoherent and coherent processes. (the energetics of which are shown in FIG. 1a) that uses two photons—a pump and a probe. The pump excites an electron into excited state S1 from ground state S0. A several hundred femtosecond delay, or more, is allowed for the decay of an excited state vibrational level into the lowest excitation level in the excited state manifold S2 via a Kasha decay process. Then a probe (or stimulated emission) beam causes the stimulated emission of a photon and the de-excitation of the electron to S3, which then rapidly decays via a Kasha decay process back to S0. The signal measured is a gain in the probe beam or loss in the pump beam. STEM techniques have been used to image molecules that absorb strongly, but do not fluoresce efficiently such as oxy-hemoglobin, deoxy-hemoglobin, melanin, cytochromes and certain drugs.

STEM is a bright field technique where a signal is added to the forward propagating probe beam. The gain in the beam is 10–4-10–7 (depending on concentration). Therefore, sophisticated electronic signal processing lock-in techniques are usually required to detect a small probe beam change. STEM imaging also uses moderate to high concentrations of molecules to image tissue at moderate to high speed. Unlike fluorescence imaging where emission occurs in any direction, the emission in STEM occurs in the forward direction. Therefore multiple scattering events are required to collect the signal at the tissue surface. STEM is best used for weakly absorbing and scattering tissues but the depth of imaging is limited and requires collection at an angle outside of the imaging aperture, eliminating the ability to do confocal imaging and degrading signal to noise ratio by collecting photons that scatter prior to reaching focus.

Multi-Photon Stimulated Emission Microscopy (MP-STEM) can be used to enhance the depth of penetration and reduce the scattering and absorption of stimulated emission photons in STEM microscopy. MP-STEM uses multiple photons for both excitation and to stimulate emission from weakly fluorescent molecules. The process of MP-STEM can reduce the focal spot size of the emitting region. When using 3 photons or more, the focal spot is reduced in size enough to cause the stimulated emission spot to be small enough to cause dipole-like backscatter emission. This occurs when the axial dimension of the emitting region shrinks to less than 50% of the stimulated emission wavelength. Dipole backscatter enables enhancement of the detected Signal to Noise Ratio (SNR) because in the back scattered direction the noise is due to the Refractive Index (RI) gradient and MIE scattering from the emission region focus in confocal microscope geometry. This is less than the forward scattered noise normally detected in STEM microscopy, or multiple backscatter STEM detection.

There are deficiencies in the use of MP-STEM.
1. It is a single point scanning system and therefore image throughput can be low. This is especially the case when it is desired to perform a 3D reconstruction of tissue being sampled.
2. The focal spot shrinkage in 2 and 3 photon MP-STEM is not small enough to provide optimal dipole backscatter.
3. Optimal focal spot reduction uses high Numerical Aperture (NA) imaging. This, typically, does not enable large standoff distances that can be desirable for in-vivo imaging.

The throughput in single point scanning MPSTEM imaging can be similar to that encountered in single point confocal fluorescence imaging. In fluorescence imaging applications Light Sheet Fluorescence Microscopy (LSFM) and Structured Illumination Microscopy (SIM) can be used to increase the throughput in imaging. Multiple image points are collected at one time and computer reconstruction can be used to rapidly create a final image. The embodiments of these techniques typically do not directly transfer to STEM microscopy because two rather than one wavelength must be used in STEM applications and STEM is a bright field technique with a high background and LSFM and SIM are dark field imaging techniques with much lower background noise.

Another stimulated emission technique that could benefit from higher throughput and lower background noise is Stimulated Raman Scattering Microscopy (SRSM). This uses stimulated vibrational transitions, rather than stimulated electronic transitions. The coherent Raman imaging techniques of Coherent Anti-Stokes Raman scattering (CARS) and SRSM have been investigated in this regard because of the ability to use intrinsic Raman vibrational signatures as label-free contrast.

Recently SRSM imaging has been further developed because of certain advantages over CARS imaging. It is substantially free from the non-resonant background present in CARS microscopy. Unlike CARS, the SRS spectrum is substantially identical to standard Raman scattering; it has shot-noise-limited sensitivity; has linear concentration dependence; has an absence of spatial coherence; and has a calculable point spread function. In the non-resonant form, it has limited susceptibility to background fluorescence.

SRSM imaging has been shown to produce images of unstained in-vitro tissue samples with similar structural identification and contrast to that achieved with standard haematoxylin and eosin tissue stains by using CH2 and CH3 vibrations of lipids and proteins. Volume stimulated Raman emission from a scanning microscope occurs in the forward scattered direction, requiring multiple scattering events to direct the light out of the tissues. Back scattered in-vivo images have been obtained with broad area detection to collect the multiply scattered photons. High resolution images with good depth resolution have not yet been shown with this approach. In addition almost all SRSM techniques use either forward scattering or multiple back scattered photons. In addition all previous techniques use single point scanning which slows down the acquisition of 3-D images.

SUMMARY

The disclosed technology relates to single and multi-photon stimulated emission microscopy used to increase depth of focus in in-vivo stimulated fluorescence imaging and SRSM and to reduce photo-bleaching of examined tissues. The disclosed technology can be applied to many applications including vibrational transitions; to image the metabolism of cells in-vivo, cerebral metabolism, as well as, stimulated emission from lipids, proteins, and nucleic acids and to provide label-less stimulated emission contrast imaging and fluorescence lifetime data from molecules in tissue with multiple component lifetimes.

In one implementation, a microscopy system comprises: a first laser emitting a first laser pulse along a first beam line, the first laser pulse being converted into an annular Bessel pump beam; and a second laser emitting a second laser pulse along a second beam line, the second laser pulse being a probe beam, the annular Bessel pump beam and the probe beam being delivered to a sample at right angles to each other allowing the annular Bessel pump beam to shrink a focal axial diameter of the second beam line thereby enabling dipole-like backscatter stimulated emission along the second beam line.

In some implementations, the pump beam can be composed of multiple points of illumination around the annular Bessel pump beam producing an optical light sheet being delivered to the sample. The optical light sheet can be focused as a line or a series of dots.

In some implementations, the second beamline can collect the dipole-like back scattered stimulated emission and focus the dipole-like back scattered stimulated emission on a confocal aperture array.

In some implementations, the microscopy system can further comprise: at least one time delay component along the second beam line for delaying the probe beam, the at least one time delay component delaying the probe beam by 0.3 ps to 5 ns relative to the pump beam.

In some implementations, the probe beam can be a single confocal, a Bessel beam spot, a continuous linear illumination, a one-dimensional array of spots or two-dimensional array of spots.

In some implementations, the microscopy system can further comprise: a galvanometer scanning system along the first beam line that scans the annular Bessel pump beam to fill in a two dimensional image in a detector located along the second beam line.

In some implementations, the microscopy system can further comprise: a galvanometer scanning system along the second beam line that scans the probe beam to fill in focal spots of the annular Bessel pump beam.

In some implementations, the microscopy system can enable reduction of an axial dimension of a stimulated emission focal spot to less than 50% of a wavelength of a stimulated emission photon.

In some implementations, the microscopy system can further comprise: an acousto-optic modulator for modulating the annular Bessel pump beam on and off.

In another implementation, a microscopy method comprising the steps of: emitting a first laser pulse along a first beam line; converting the first laser pulse into an annular Bessel pump beam; emitting a second laser pulse along a second beam line, the second laser pulse being a probe beam; and delivering the annular Bessel pump beam and the probe beam to a sample at right angles to each other thereby allowing the annular Bessel pump beam to shrink a focal axial diameter of the second beam line thus enabling dipole-like backscatter stimulated emission along the second beam line.

In some implementations, the pump beam can be composed of multiple points of illumination around the annular Bessel pump beam producing an optical light sheet being delivered to the sample. In some implementations, the optical light sheet can focused to one of a line or a series of dots. In some implementations, the second beamline can collect the dipole-like back scattered stimulated emission and focus the dipole-like back scattered stimulated emission on a confocal aperture array.

In some implementations, the microscopy can further comprise the step of: delaying the probe beam by 0.3 ps to 5 ns relative to the pump beam. In some implementations, the probe beam can be a single confocal, a Bessel beam spot, a continuous linear illumination, a one-dimensional array of spots or two-dimensional array of spots. In some implementations, the microscopy can further comprise the step of: scanning the annular Bessel pump beam along the first beam line to fill in a two dimensional image in a detector located along the second beam line.

In some implementations, the microscopy can further comprise the step of: scanning the probe beam along the second beam line to fill in focal spots of the annular Bessel pump beam.

In some implementations, the microscopy system can enable reduction of an axial dimension of a stimulated emission focal spot to less than 50% of a wavelength of a stimulated emission photon. In some implementations, the microscopy can further comprise the step of: modulating the annular Bessel pump beam on and off.

In one implementation, a microscopy system can comprise: a first laser emitting a first laser pulse, the first laser pulse being a pump beam; a second laser emitting a second laser pulse, the second laser pulse being a probe beam; time delay components for delaying the probe beam, wherein the time delay components delay the probe beam by 0.3 ps to 5 ns relative to the pump beam; two separate optical beam lines with appropriate delays to deliver the beams to the sample at right angles to each other. One beamline, called Beamline 1 produces an annular Bessel pump beam that can be focused to a line or a series of dots in an optical light sheet in the sample. There is a galvanometer scanning system that scans the annular Bessel pump beam to fill in a two dimensional image in the detector in the second beam line. The second beam line, called beamline 2, produces a probe beam that includes a single confocal or Bessel beam spot, a continuous linear illumination or a 1 dimensional or 2 dimensional array of spots that is confocal with the first beamline pump stimulation focus.

The second beamline probe beam can produce stimulated emission. There can be galvanometer scanning systems in the second beam line that fill in the array of spots and scan in the orthogonal direction to produce a full image. The second beamline collects the direct dipole back scattered stimulated emission light and focuses this light on a confocal aperture or an array of confocal apertures in front of a differential or phase sensitive imager array designed for detecting signals with high dynamic range. For single photon excitation microscopy, either for electronic or vibrational transitions, a second annulus of graded phase of pump illumination may be added to reduce the secondary pump Bessel beam modes along the beamline 2 optical axis. This microscope configuration is called Orthogonal Beam Stimulated Emission Microscopy (OB-STEM).

The Point Spread Function (PSF) of a single or multiphoton stimulated emission microscope is the product of the pump PSF to the power of the number of photons used to excite the transition, multiplied by the probe PSF multiplied by the power of the number of probe photons used to stimulate the transition. In the (OB-STEM) disclosed here the focal spot dimension perpendicular to the light sheet which is along the optical axis of the second beam line, in conjunction with the probe focal spot makes the axial dimension of the probe emission region small enough to enable stimulated emission dipole backscatter. This can be accomplished by use of a single or multiphoton Bessel stimulated emission beam pump in combination with orthogonal single photon or multiphoton stimulated emission. The combination of multiphoton light sheet illumination and stimulated emission enables reduction of the axial dimension of the stimulated emission focal spot to less than 50% of the wavelength of the stimulated emission photon; wherein the reduced focal spot size enables the stimulated emission having dipole-like backscatter; that is collected by an a single or array detector for enabling imaging of the dipole-like backscatter. In some implementations the emission spots can be made even smaller by using structured illumination in both or either of the pump light sheet and the probe beam. In these cases the pump beam is composed of multiple points of illumination around the Bessel beam producing a light sheet lattice. The probe beam can be formed from a single confocal or Bessel beam spot, a linear array of dots formed from an interfering structured illumination approach or a two dimensional array of dots by imaging a mask or reflection from a Structured Light Modulator (SML). These approaches produce higher resolution imaging.

In some implementations, at least two photons can be used for both excitation and stimulation of a targeted molecule. In some implementations, the stimulated emission of the targeted molecule can be red shifted by enabling the excited state fluorescent electronic transition to the ground state vibrational levels to occur via a multiphoton stimulated transition of the molecule; where the sum of the energies of the multiple stimulated emission probe photons is resonantly about equal to the energy of the fluorescent transition.

In some implementations, the stimulated emission of the targeted molecule can be used to measure a metabolic state of cells deep within tissues via a measurement of a concentration of metabolic cofactors NADH and NADPH, in both free and bound states. In some implementations, the multiphoton stimulated emission occurs in proteins, or nucleic acids and is used as image tissues without stain. In some implementations the stimulated emission is used to measure the concentrations of melanin and its derivatives.

In some implementations, the time delay components can include an optical switch in the probe beam line to switch the probe beam between at least two delay lines. In some implementations, the optical switch can allow at least two different temporal delays between the pump beam and the probe beam so that molecular fluorescence lifetime can be calculated. In some implementations, the optical switch can be a Mach-Zehnder interferometer.

In some implementations, the combined laser pulses can be used to excite an electron into an electronic excited state that emits stimulated emission from its lowest energy excited state level.

In some implementations, the microscopy system can further comprise: an acousto-optic modulator for modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

In another implementation, a microscopy method can comprise the steps of: emitting a first laser pulse, the first laser pulse being a pump beam; emitting a second laser pulse, the second laser pulse being a probe beam; delaying the probe beam, wherein the time delay components delay the probe beam by 0.3 ps to 5 ns relative to the pump beam; combining the pump beam and the delayed probe beam into a combined laser pulse, the combined laser pulse having a reduced focal spot size; delivering the combined laser pulse to a focal spot in a focal plane, wherein the reduced focal spot size of the combined laser pulse initiates a stimulated emission of a targeted molecule, the stimulated emission having dipole-like backscatter; and enabling imaging of the dipole-like backscatter.

In some implementations, the microscopy method can further comprise the step of: modulating the pump beam on and off. In some implementations, the collection apparatus can generate an imaging signal corresponding to a gain in intensity of the probe beam computed as the difference between the combined laser pulse with the pump beam on and the combined laser pulse with the pump beam off.

Advantages of the disclosed technology include an enhancement of the speed of image acquisition of back scattered stimulated emission by acquiring multiple points at for each pair of laser pulses, use of lower NA objectives for delivery of pump and probe photons to the sample increasing working distance of the objective to sample; reduction of the noise by using dipole emission enabling the detection of lower concentrations of molecules compared to traditional stimulated imaging; and increasing speed of imaging for use in research and clinical medicine.

BRIEF DESCRIPTION OF THE DRAWINGS

FIG. 1a is a graphical depiction of an energy diagram of 1 photon STEM;

FIG. 1b is a graphical depiction of an energy diagram of 2 photon excitation and 1 photon stimulated emission STEM;

FIG. 1c is a graphical depiction of an energy diagram of MP-STEM (2pse);

FIG. 1d is a graphical depiction of an energy diagram of 3 photon MP-STEM (3pse);

FIG. 5 is a table showing 1 photon, 2 photon, 3 photon and 4 photon pump excitation and probe stimulated emission wavelengths for biological molecules;

FIG. 6a is a diagram of the annular Bessel pump beam

FIG. 6b is intensity distribution in radius, z plane

FIG. 6c is intensity distribution in the x, y plane

FIG. 6d is the intensity distribution along the pump beam axis

FIG. 6e is the intensity distribution along the long z axis of the pump beam

FIG. 11a is an illustration of pump structured illumination;

FIG. 11b is an illustration of probe structured illumination;

FIG. 12 is an energy level diagram for a stimulated Raman vibrational transition;

FIG. 13a is a view of the 2 annulus phase Bessel filter used for single filter stimulated fluorescence and stimulated Raman scattering;

FIG. 13b is a view along the z axis of the Bessel excitation beam; and

FIG. 13c is a view of the secondary lobes removed along the x axis.

DETAILED DESCRIPTION

Figure 2:
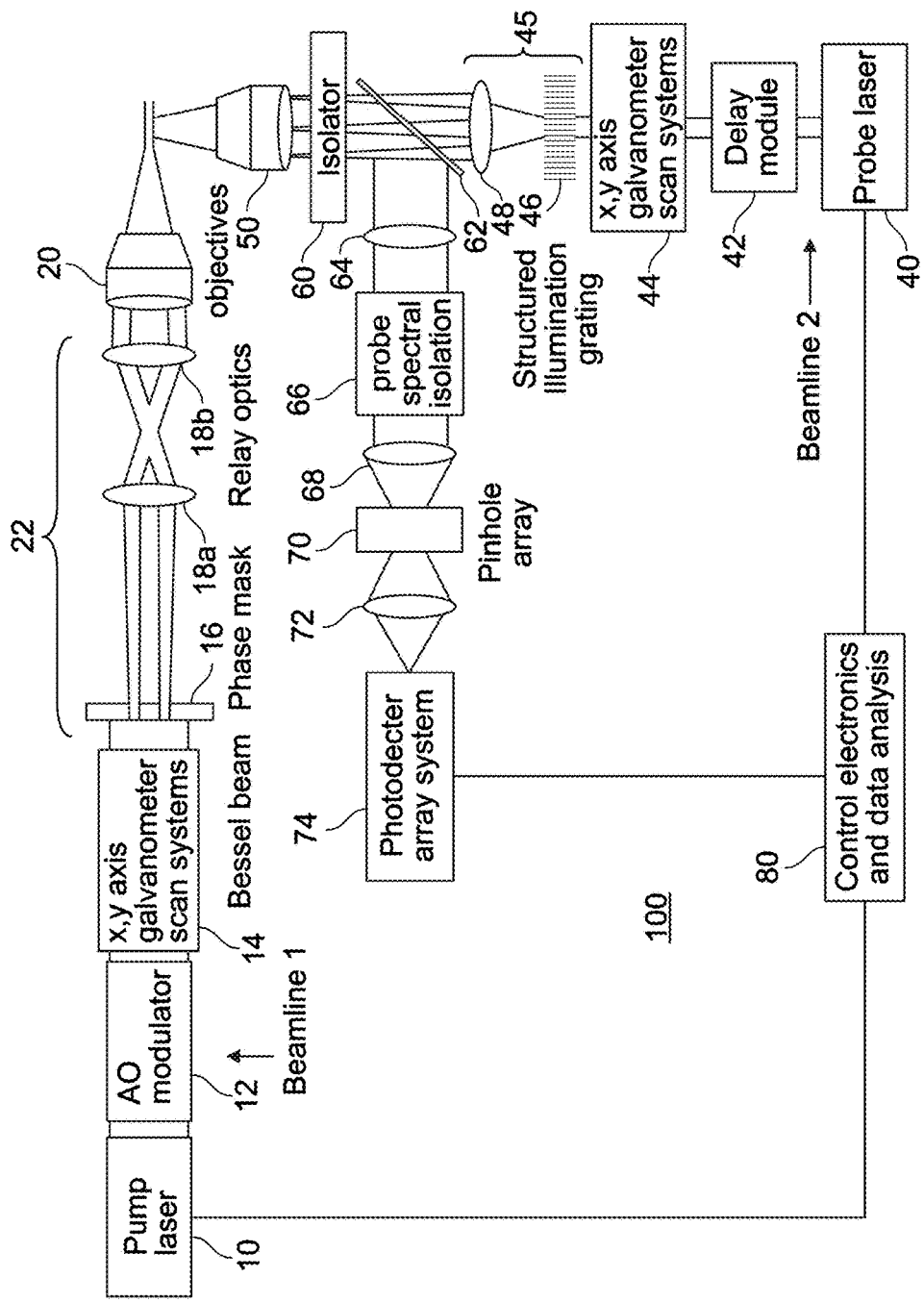
FIG. 2 is a block diagram of an example of a system used with the disclosed technology.

The disclosed technology is related to systems and methods that enable deep tissue imaging through the use of 1-4 pump photons to excite a molecule of a sample tissue, through one or more virtual excited states. In addition, stimulated emission photon beams with photons of 100%, 50%, 33% or 25% of the energy difference of the lowest level excited state and an excited level in the ground state manifold can be used to stimulate the emission of 1, 2, 3, or 4 photons that can be added to a backscattered stimulated emission beam. This emission can occur as the excited state electron is moved from the excited state to the ground state manifold through one or more virtual energy levels via a single or multi-photon stimulated emission process.

The disclosed technology uses single or multi-photon excitation with a Bessel (annular) beam to shrink the focal axial length of the orthogonal stimulated emission optical beamline to subwavelength probe photon (or stimulated emission photon) dimensions. This shrinking of the focal axial diameter enables dipole-like backscatter stimulated emission along the orthogonal stimulated emission beam direction and direct ballistic photon backscatter imaging from deep within tissues.

The disclosed technology can be used to measure the concentrations of both fluorescent and poorly-fluorescent states of the enzyme cofactors NADH and FAD, map the metabolic state of a tissue under study and map many chromophores that are not fluorescent such as drugs, nucleic acids and proteins.

The disclosed technology can also enable label-free in-vivo stimulated auto-fluorescent, or Stimulated Raman, imaging for medical research, endoscopy, and dermatology and to define clear margins in cancer surgery using low and high quantum efficiency emitters. In one implementation, Multi-Photon Stimulated Fluorescent (MP-STEM) can enable enhanced depth of penetration of imaging of drugs, metabolic metabolites and direct fluorescent imaging of DNA, RNA and protein fluorescence in living tissue. That is, the MP-STEM process enables collection of direct back scattered photons into the imaging apertures of a confocal array from a dipole-like emission created using 1, 2, 3 and 4 photon stimulated emission processes. MP-STEM enables deep tissue imaging of weak, as well as, strong, fluorescent molecules emitted in both the visible and UV regions of a spectrum. In some implementations, MP-STEM can be a multiphoton process for both excitation and generation of stimulated emissions, which in turn, red shifts stimulated emission photons for enhanced imaging.

A single fluorophore emits stimulated emission into the backward illumination and forward propagating stimulated emission modes with equal probability. This occurs, in part because the fluorophore is small relative to the optical wavelengths of the stimulating photon. However, it is known that as stimulated emission gain length of a volume of emitters increases, dipole backscatter quickly decreases. In a microscope the gain in the stimulated field may be small, due to the small focal spot and low concentration of molecules. However, as the probe beam propagates along the forward direction through the focal spot the stimulated emission photons add in phase to the stimulating beam, increasing the coherent traveling field. The stimulated emission in the back propagation direction adds out of phase as the incident stimulating beam propagates forward. Thus as the gain medium length increases, the back scattered stimulated emission photons from axially spatially separate fluorophores add with a continuously changing phase and may destructively interfere over standard confocal microscope axial focal length. Thus the backscattered stimulated field quickly decreases over sub-wavelength dimensions which are a fraction of an axial length, even for very high NA microscope objectives.

Figure 10:
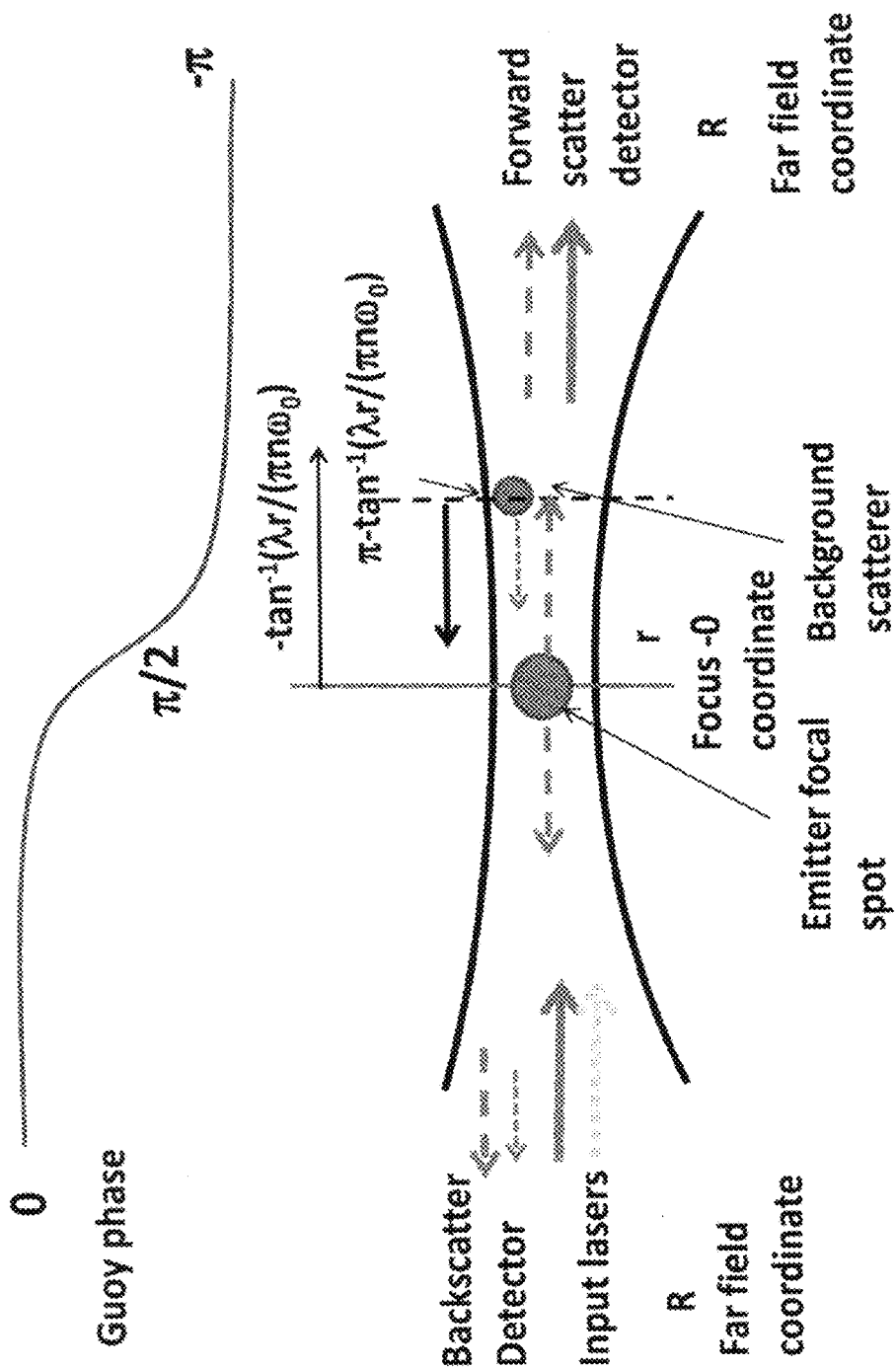
FIG. 10 is an illustration of a direction of the stimulated emission in normal sized focal spots and LS-STEM spots reduced to <50% of the probe wavelength in the axial direction and is an illustration of a Position of Index of Refraction backscatter relative to focus and the relationship to Gouy phase.

It is desirable to maximize the direct back scattered signal. The background noise characteristics in STEM imaging of dipole emitters are different in the forward and back scattered directions. In the forward direction the background noise can be primarily from photons in the excitation probe beam and can be more intense than accompanying probe stimulated emission. This is also the case for collection of multiply scattered epi collected signals. For backward propagating dipole emission in confocal microscope geometry, the background noise comprises back scattered probe photons from within the focal volume of the microscope, and multiple scattered photons that enter into the confocal aperture system. The direction and sources of collected signal and noise photons is shown in FIG. 10.

Most back scattered photons within the microscope focal spot come from refractive index (RI) gradients in the focal volume. This noise can be about $5 \times 10^{-4}$ of the incident beam, at the interface of cytoplasm and cell nuclei. Thus backscatter noise can be less than forward noise, reducing the incident flux for STEM imaging. In addition, by reducing the noise, lock-in, differential or phase based data collection techniques may not be required.

Figure 9:
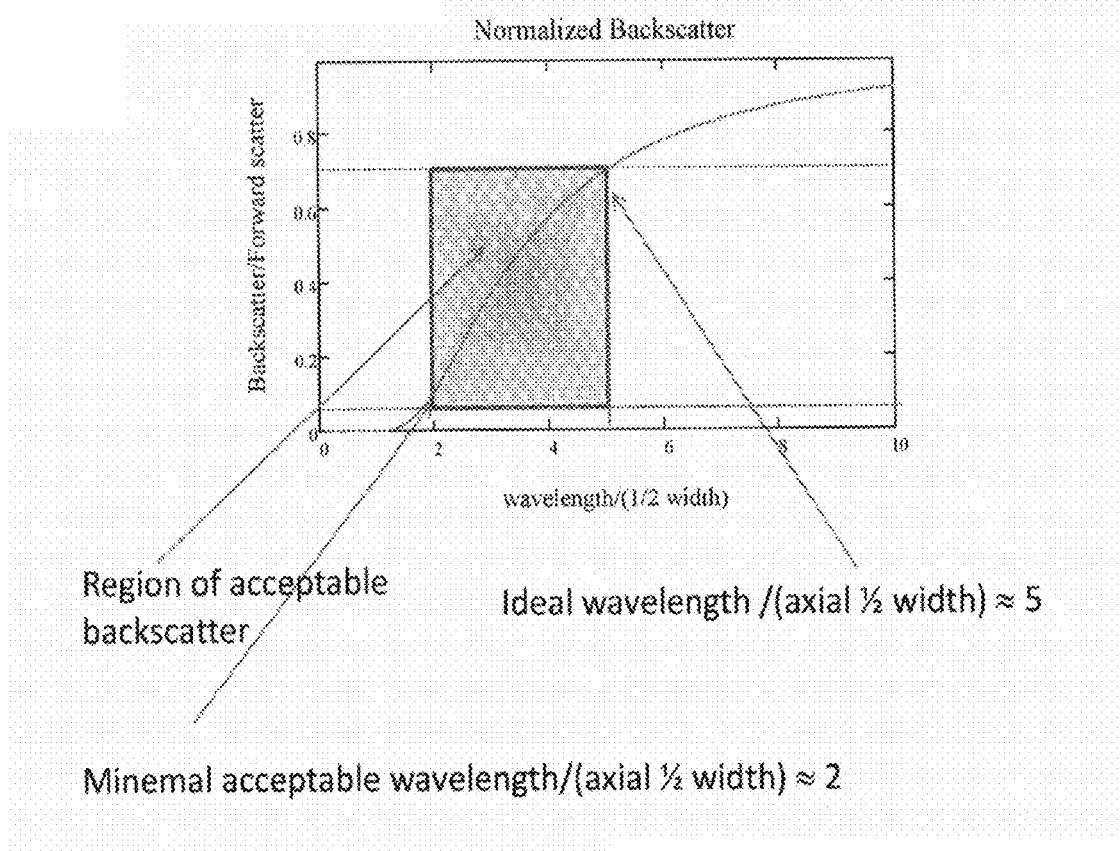
FIG. 9 is a graphical depiction of a ratio of back scattered to forward scattered stimulated emission as a function ratio of emission wavelength to emission axial ½ widths.

FIG. 9 plots the ratio of back scattered to forward scattered stimulated emission as a function the ratio of emission wavelength/(emission axial focal spot ½ width). When the axial probe length is less than ½ of the wavelength, the backscatter is adequate to use for imaging applications. The optimal axial length is about ⅓ of the probe wavelength for a volume of emitters. Smaller focal spots result in a smaller number of stimulated emission photons, unless emitting molecules are concentrated in a smaller area than the emitting spot.

In co-pending U.S. patent application Ser. No. 14/881, 701, hereby incorporated by reference, 2 photon stimulated emission in conjunction with a third beam—the donut beam was used to reduce the focal spot to dimensions of the axial focal spot to less than 50% of the probe wavelength to cause stimulated emission in the back scattered dimension.

In co-pending U.S. patent application Ser. No. 14/949, 612, hereby incorporated by reference 2-4 photon are used both for pumping the excited state and stimulated emission to reduce the focal spot size to dimensions of the axial focal spot to less than 50% of the probe wavelength to cause stimulated emission in the back scattered dimension.

This disclosure includes the following:
1. A method and system using 2 microscope objectives at right angles. One beam path is used to create a Bessel annular beam to enable a thin single or multi-photon pump illumination at the extended focal region of the pump microscope objective. The second beam path is used for confocal delivery of a stimulated emission photon beam to the microscope focus in the form of a single confocal or Bessel beam spot, a line, or a one or two dimensional array of spots. The stimulated emission beam can be used to enable 1-4 photon stimulated emission. The second beamline is also used to acquire the dipole-like stimulated emission backscatter though a single aperture or an array of confocal apertures in front of a differential and/or phase detection detecting photodiode array. When 2 or more photons are used for stimulated emission to cause stimulated fluorescent emission that is red shifted compared to the standard blue or UV fluorescent emission, this is called Multi-Photon Stimulated Emission (MP-STEM) imaging.
2. The use of structured illumination in either the probe beamline or the pump beamline or in both the probe and pump beam lines. Structured illumination using a Bessel beam in the form of an array of spots can deliver an optical lattice array of spots in the form of a light sheet pump beam. Structured illumination in the probe beam can deliver a linear grating or two dimensional grating to the same focal area in the sample that is illuminated by the pump beam. These implementations can enable higher resolution imaging.
3. The techniques in 1 or 2 can be used to image 1 photon or multiphoton direct back scattered stimulated emission from proteins, nucleic acids, drugs and molecular cofactors in vivo without the use of stains.

The energetics of pump and a probe beams used in stimulated fluorescent emission (STEM) imaging are shown in FIG. 1a. The pump excites an electron to state S1 from S0. The excited electron decays to the lowest energy excited state S2 via a rapid Kasha decay process decay process. Then a probe (or stimulated emission) beam causes the emission of a photon and the de-excitation of the electron to S3, which then rapidly decay via a Kasha decay process back to S0.

Multiphoton excitation, as shown in FIG. 1b, is widely used in fluorescent microscopy to enhance the depth of penetration of excitation light and to reduce the photobleaching of molecules positioned out of focus.

Multiphoton stimulated emission takes advantage of the fact that the Einstein absorption and stimulated emission coefficients are similar. Multiphoton stimulated emission red shifts the blue and UV fluorescent emission into the green, red or near IR. Two photon stimulated emission (2pse) energy levels are shown in FIG. 1c. FIG. 1d shows the energetics of three photon excitation and three photon stimulated emission (3pse). Using 2 or more photons for both excitation and stimulation is called Multiphoton Stimulated Emission (MP-STEM) microscopy.

MP-STEM is distinct from all previous types of multiphoton microscopy. Each excited electron transition to the ground state vibrational manifold adds two stimulated emission photons to the probe beam used to measure gain in 2pse processes. Each photon has about ½ the energy of the single photon transition. Three photons are added to the probe beam in a 3pse process for each molecular stimulated emission. Each photon in 3pse has about ⅓ the energy of the single photon transition.

Use of MP-STEM microscopy can enable direct in-vivo tissue imaging of the UV fluorescence from proteins and nucleic acids by shifting the emission into the green or red, as shown in the table in FIG. 5. This creates the opportunity for non-stained tissue contrast imaging at high resolution.

In the system disclosed here, for convenience called Light Sheet STEM (LS-STEM), there are two Point Spread Functions (PSF) that contribute to the final system response function called $PSF_{st}$. The basic system is shown in FIG. 2. One PSF is from the Bessel beam pump illumination from the first beam line and is called $PSF_{pu}$. The other is from the second beamline or pump beamline and is called $PSF_{pr}$. For the system $PSF_{st} = PSF_{pux} PSF_{pr}$.

The disclosed technology uses Bessel beam illumination to produce light sheet beams with large depths of focus. These Bessel beams are produced by shining a Gaussian laser beam through an annular aperture 16 as shown in FIG. 2 and FIG. 6a. The Gaussian laser beam is placed through a relay lens system 18a, 18b to create a light sheet, prior to focusing the beamline 1 through a microscope objective 20. This is shown schematically in FIG. 2 as the Bessel beam generator 22. In some implementations, the intensity of the light sheet can be increased by preconditioning the laser beam into an annulus by an axicon-lens lens pair. Light sheets of optical lattices can be generated by using an array of illumination spots around an annulus as shown in FIG. 11a and as described in Chen et al, Science Vol. 346 Issue 6208 page 439, hereby incorporated by reference. Various other illumination patterns are possible and can be generated using a Spatial Light Modulator (SLM).

Figure 3:
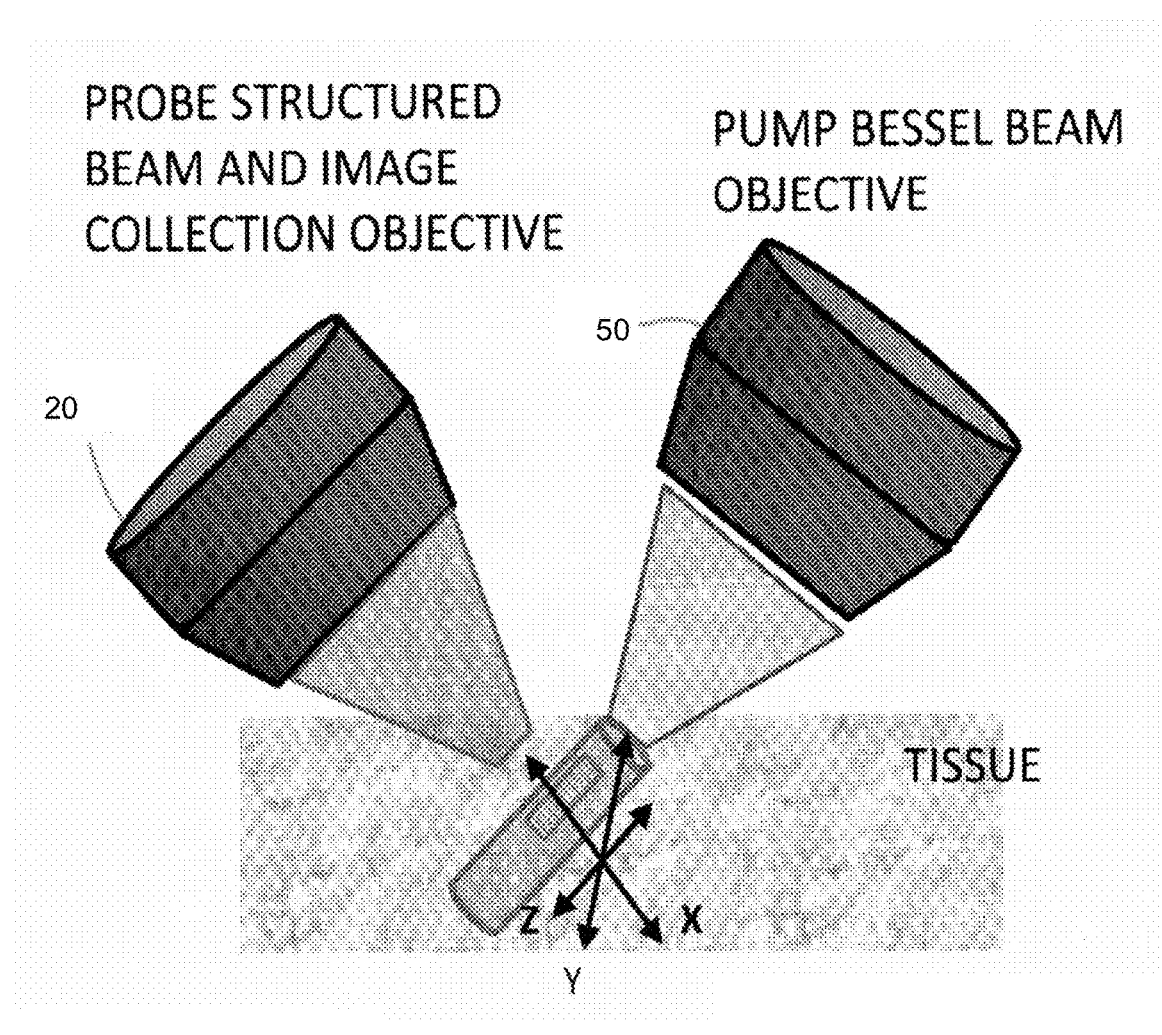
FIG. 3 is a block diagram of an example of microscope objectives focal volume used with the disclosed technology.

The coordinate axes of a focus area are shown in FIG. 3. The optical axis of the pump beamline is z, and the optical axis of the probe/detection beamline is y. The x axis is the one axis transverse to both beamlines.

In FIG. 6, the inner and outer Numerical Apertures of the illumination annuluses are 0.50 and 0.53 respectively and described in Zhang et al, Optics Express, Vol. 22, No. 10 p 12398 (2014) hereby incorporated by reference. FIG. 6 reviews the performance of one $PSF_{pu}$. In this figure a long focus along the axial dimension of the pump beam labeled z is illustrated in the focal region of the LS-STEM microscope focal region shown in FIG. 3. FIG. 6e shows that over the central 16 microns along the z axis the illumination is substantially flat. As shown in FIG. 6c at z=0 there is a small central spot produced. FIG. 6d shows a calculation of the intensity of the $PSF_{pu}$ that reveals the multiple side lobes that are produced by using Bessel beam illumination. The multiple Bessel side lobes can reduce the dipole backscatter in STEM. These side lobes are reduced by using two or more photons for illumination, or by using a secondary annulus of illumination that destructively interferes with the outer rings, alone the probe beamline optical axis.

The central lobe in FIG. 6d, for a pump wavelength of 635 nm has a ½ width of about 385 nm or about 60% of the illumination wavelength. This half width is along the y-axis, (the axial dimension of the probe beam illumination). The lateral width can be reduced further by using a higher NA Bessel; this can come at an expense of a shorter axial extension and therefore a smaller field of view. FIG. 6e shows that over the central 16 microns along the z axis the illumination is substantially flat. In single point spot scanning OP-STEM systems, there is no problem with reduction in the length of the Bessel beam axial length. In these cases NA's of 0.6 or more would be used.

If the Bessel beam uses two photon pump illumination, the side lobes of the Bessel beam can be reduced and the half width of the pump beam illumination can be reduced to ~36% of the pump beam wavelength and if 3 photon excitation is used for pump illumination then the pump beam illumination wavelength can be about 22% of the pump wavelength. This is a reduction of the axial dimension of the probe, and with the reduction in the secondary lobes enables direct dipole back scattered stimulated fluorescence from the probe beam delivered by the second beamline.

The $PSF_{pr}$ for the second beamline is determined by the NA of the microscope objective 50 in that the objective 50 delivers the probe light and collects the back scattered stimulated emission as shown in FIG. 2. The $PSF_{pr}$ also depends upon the illumination structure delivered by beamline 2. In some implementations, lower NA objectives can be used for the probe beam. Probe beam NA objectives in the 0.3 to 1.1 region can achieve dipole stimulated emission backscatter. The pump beam objective 20 may produce a stimulated emission single confocal spot, or use annular illumination to produce a Bessel beam. Using a Bessel beam may produce higher resolution than with a lower NA objective.

When the emission spot is reduced to less than 50% of the probe wavelength along the optical axis, dipole-like stimulated emission with both a forward and backward scattered lobe starts to occur as shown in FIG. 9. Backscatter occurs because of the lack of destructive interferometric cancellation of backscatter in gain lengths shorter than 50% of the emission wavelength. Direct backscatter enhances the recorded signal to noise ratio (SNR) of images because of reduced backscatter noise compared to forward propagating addition stimulated emission of the forward propagating probe beam.

MP-STEM systems operate near saturation where typically at most 50% of the excited molecules at focus will emit stimulated emission gain photons. STEM lasers systems have operated with very high repetition rate systems ~80 MHZ (12 ns pulse repetition rate) to build up SNR for lock-in detection of single photon STEM emission from rapid decay species, with imaging acquisition in the forward scattered direction or for multiple backscatter for collection in the epi direction. (Standard Multi-photon fluorescent systems operate at slower repetition, put higher intensities (near saturation) at focus.) At high repetition rates, near saturation local tissue heating can be an issue. Therefore lower repetition rates can be desired. However, in the back scattered direction repetition rates can be reduced because of the reduction in background photon noise.

At high repetition rates in MP-STEM systems, the excited state of long lived fluorophores may not be fully depleted when the next pump-probe pair arrives. For molecules with fluorescence lifetimes of >2 nsec, such as NADPH, this can be a problem, and lower repetition rates are required.

Above 1000 nm the photon damage limit in tissues is higher, enabling higher intensity focal spots. The focal spots can be smaller enabling enhanced dipole backscatter. Fiber lasers can be used for excitation and stimulated emission. Use of fiber lasers reduces the cost of system construction, and enhances ease of use. Tissue dispersion is lower above 1000 nm than below, making achieving a more precise focal spots with short pulses easier to achieve.

Below 950 nm NIR enhanced diode arrays can be used to collect back scattered stimulated emission images. Use of photon wavelengths longer than 950 nm typically requires the use of detectors that are not silicon based. Array detectors are available with photodetectors formed from SiGe, InGaAs and HgCdTe, that can cover the wavelength band from 950 nm-1800 nm.

The fluorescent molecule energy level diagrams for STEM imaging are outlined in FIG. 1a. In STEM, two laser beams at the pump frequency, $\omega_{pu}$, and probe frequency, $\omega_{pr}$, are coincident on a sample as shown in FIG. 1a. The pump photon excites an electron into state S1. This exited stated decays via a Kasha process to the lowest level excited state S2 in 0.1-1.0 ps. The probe frequency photons have appropriate energy to drive an excited electron into a high level excited state in the ground state manifold S3 as shown FIG. 1a. The electron in the ground vibrational excited state then losses energy as it decays into the lowest ground state S0 by another Kasha process.

FIG. 1b shows the excitation of the fluorescent molecule into the electronic excited state via a 2-photon excitation process. The electronic excited state excitation occurs through a virtual level intermediate, which has a femtosecond lifetime. Therefore, the two excitation photons arrive close in time, which requires high photon intensities and occurs at high probability at the focal spot of the microscope, using high power picosecond or sub-picosecond laser pulses. Advantages of 2-photon excitation can include 1) the lower energy photons used in 2-photon excitation generally have lower absorption and scattering cross-sections than the 1-photon excitation energies, enabling deeper tissue excitation; 2) the requirement of high intensity of excitation enables emission mostly from the focal volume; 3) the lower energy photons produce less photo-bleaching molecules in the focusing and defocus cones of the microscope objective, providing less damage to the tissue being imaged.

FIG. 1c shows the energetics of 4 photons in a MP-STEM process. In this case 2-photon excitation and 2-photon stimulated emission are used. The addition of 2-photon stimulated emission along with 2-photon excitation is enabled by the approximate equivalence of the Einstein absorption and stimulated emission constants. The system is efficient when both the excitation and stimulated emission processes operate near saturation. This process is called 2 photon stimulated emission (2pse) MP-STEM.

The addition of 2-photon stimulated emission has several advantages including; 1) less absorption, and scattering of stimulated emission photons, enabling rapid and deeper stimulated fluorescent imaging; 2) enables forward and back scattered STEM imaging of fluorescent transitions in the UV, which normally would not be observable because of tissue absorption; 3) enables imaging of short lived fluorescent molecules such as DNA and proteins.

FIG. 1d shows the energetics of a 6 photon MP-STEM process, which is also disclosed here. In 3-photon excitation and 3-photon stimulated emission there are 2 intermediate virtual levels. Therefore the required incident laser intensities can be higher than in 2 photon excitation and 2 photon stimulated emission. However, the process enables incident photons in the near infrared, for UV or blue fluorescent transitions from deep within tissue. This process is called 3 photon stimulated emission (3pse) MP-STEM. Four photon stimulated emission (4pse) MP-STEM is also possible.

It should be noted that it is possible to mix pumping or probing with n photons with pump or probe beams with n−1 photon processes. Two photon excitation and 3 photon stimulated emission can be used to get a clean back scattered signal.

Referring to FIG. 2, a microscopy system 100 can have a pump laser 10 being focused along beamline 1 and a probe laser 40 being focused along beamline 2. Beamline 1 and beamline 2 are focused to a confocal region in a sample. The pump and probe beams can be produced by fiber lasers, or solid state lasers such as a Ti:Sapphire laser. The lasers beam photons can be in the green through near infrared regions of the optical spectrum (500-1840 nm).

Beamline 1 can include an Acousto-optic Modulator 12 that turns the pump laser on and off during image scanning thereby enabling lock-in or differential stimulated emission detection. Further Beamline 1 can include a galvanometer scanning module 14 that scans the z axis line illumination to the y axis to create a 2-dimensional image and in the x axis to create a 3-d volume of excitation. Beamline 1 also can include a phase mask 16 that converts the pump laser beam into an annular beam that enables focusing of a Bessel beam to a focal region. The Bessel beam can then be converted to a light sheet by a cylindrical lens assembly 18a, 18b. In FIG. 2, the combination of the annular aperture 16 and the relay lens assembly 18a, 8b is called a Bessel Beam Generation module 22. The focal beam produced by beamline 1 has a narrow and long focal region as shown in FIG. 6b.

Beamline 2 can include a delay module 42 that can delay the probe beam from 100 s of femtoseconds to multiple nanoseconds after the arrival of the pump beam. The delay in the delay module 42 can be generated by a delay in the probe beamline or by electrical delay in a trigger circuit used in time synchronization of the pump and probe pulses. The pathlengths of the probe can initially be adjusted by placing an optical delay with movable mirrors in the laser beams, as illustrated for the probe beam. Long time delays can be used when the system is used to measure fluorescence lifetime of biomolecules.

Multiple delays can be used to measure a multi-component exponential delay curve. One can measure multiple delays at each pixel as the laser is scanned, in order to enhance image acquisition speed. This is accomplished by using an optical switch (not shown) in the probe beam line to switch the pulse between two or more delay lines.

Beamline 2 can also include a galvanometer scanning module 44 capable of filling in the array of spots of the light sheet and scan in the orthogonal direction to produce a full image.

The probe beam is delivered by beamline 2 as a linear focus that is confocal with the pump focus of Beamline 1. The pump focus can be composed of a solid line or a series of dots enabled by a Structured Illumination Module 45. The structured illumination module 45, if used, can be composed of a transmission grating 46 and isolator 48 that can collect the +/1 first order and 0th order diffracted beam as shown in FIG. 11b and described in Gustafsson et al. Biophys J Vol. 94 pages 4957-4870 (2008), hereby incorporated by reference. In an alternate implementation, a spatial light Modulator can be used to produce a linear spot illumination profile from a probe laser. It should be noted the probe beam may be a single confocal microscope spot or a Bessel beam illumination.

The back scattered stimulated emission probe light can be collected in the second beam line and can be focused through a pinhole array 70 or a linear slit and then on to one to a linear 1D or 2D differential or lock-in photon diode array 74, or a single photodiode. If a linear detector array 74 is used the sample must move under the microscope objectives or the light focus must be adjusted to fall on the 1D array, as the pump beam is scanned in the y axis plane. The probe beam must also be scanned by the galvanometer system 44 in Beamline 2. If a 2D array is used, both the pump and probe beams are moved by galvanometer scan modules 14, 44 to maintain a confocal linear region that is moved to fill in the 2-D array. The image must be dithered by the galvanometer system to fill in the pinhole images along the z axis. A sample to be investigated is located in or near the focal volume of the two beamlines. In addition Beamline 2 includes an optical delay module 42 to control the time of arrival of the probe pulse relative to the pump pulse.

The data is collected and the laser timing and diagnostics are controlled by a control electronics module 80.

When MP-STEM is used for deep tissue imaging, the small refractive index and thermal gradients in the tissue can reduce the focal intensity of the pump beam on target. In this case an optical aberration correction system can be used to enhance the focal power. These systems have been used in CARS and Multiphoton fluorescent microscopy systems.

The stimulated emission microscope system 100 described here is a bright field imaging system and the intensity of the background probe radiation can be calibrated on a rapid time interval cycle. Therefore, the pump Beamline 1 has an optical modulator 12 that turns the pump beam on and off enabling collection of probe beam photons with and without probe beam gain from stimulated emission. This optical modulator 12 can be an acousto-optic modulator 12.

Figure 4:
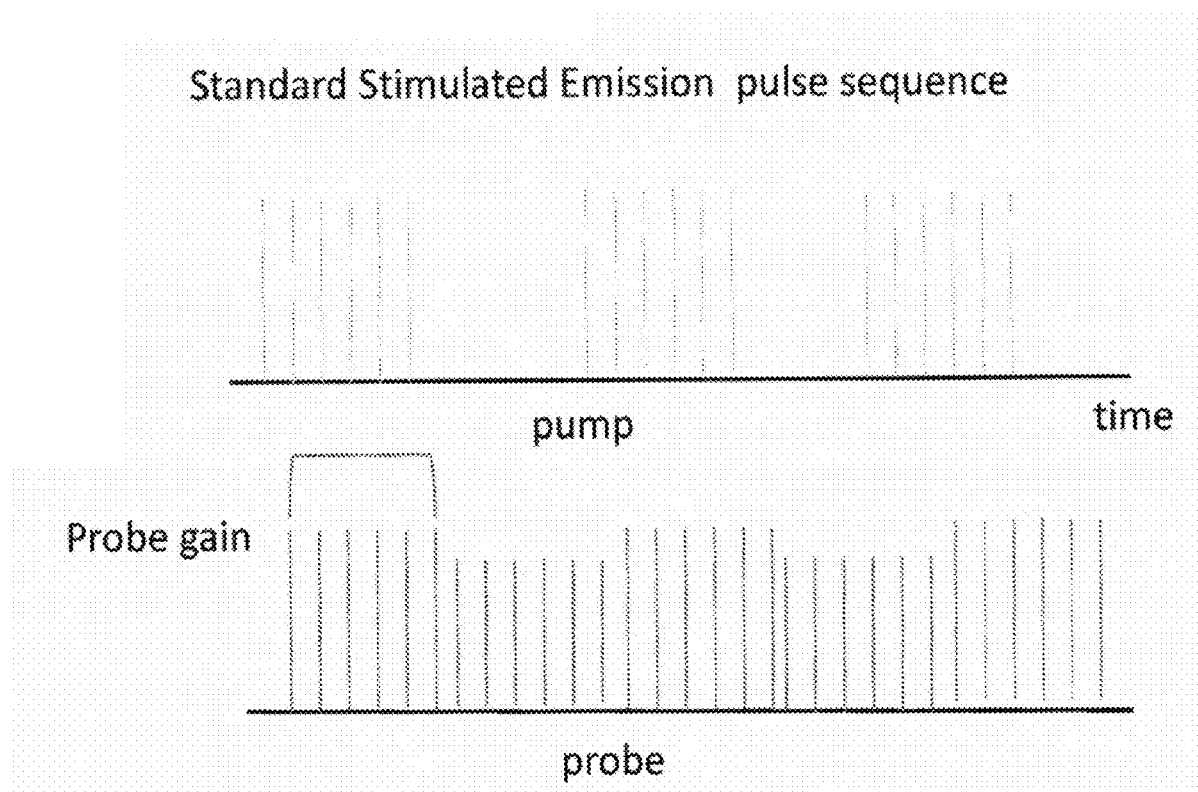
FIG. 4 is a graphical depiction of a time sequence for pump and probe beams.

The time sequence of the pump and probe beams are shown in FIG. 4. The pump is turned on for a series of pulses to measure gain and turned off to measure the bright field single without gain. The repetition rate of the pump and probe can be about 10-20 MHz for MP-STEM systems. For single photon fluorescence STEM or stimulated Raman STEM systems repetition rates of up to 80 MHZ may be used. The photodetector array system 74 can be a lock-in array amplifier system and can measure the envelope frequency of the pulse train at about 1-5 MHz. It should be noted that because of the reduced back scattered noise high dynamic range non lock-in detection arrays can also be used for image acquisition.

In FIG. 2, the stimulated signal can be collected by a detector 74 in the back scattered direction. The probe wavelength and stimulated emission back scattered wavelength are substantially the same. Thus changing polarizations are used to isolate the back reflected signal. The probe beamline thus has an isolation module 66 that controls back reflected photon polarization to collect the back scattered photons. The isolation module 66 can be composed of a Faraday rotator and a waveplate, and the pickoff mirror 62 for the beam line is a polarization dependent reflector. For very deep tissue imaging using dipole back scattered emission, the signal is collected in the imaging aperture and with a confocal pinhole array, in front of the collection detector array 74, as shown in FIG. 2. This isolates multiple scattered photons.

The time sequence of pump and probe beam signals are shown in FIG. 4. The imaging signal corresponds to the stimulated gain in intensity of the probe beam, computed as the difference between the probe signal from the fluorescent molecular excited state populated by the pump beam, and the un-excited molecular probe signal with the pump beam off. Standard interference filters can be used to separate pump and probe photons because they are separate in wavelength by >10 nm.

FIG. 5 provides a table of pump and probe wavelengths for 1, 2 3 and 4 photons for both excitation and stimulated emission in STEM and MP-STEM for proteins and DNA as well as two electron transport cofactors NADH and FAD, widely used in cellular metabolic imaging. For proteins and DNA, the single photon pump and probe wavelengths are in the deep UV and cannot be imaged efficiently and usually without tissue damage in-vivo. With 2-photon excitation and emission MP-STEM imaging the wavelengths are moved into green and red, suitable for imaging with a depth of about 100 microns. Using 3-photon emission MP-STEM imaging, proteins and DNA can be imaged in near infrared, at depth of 300 microns or more.

The electron transport cofactors NADH and FAD can be imaged in the near IR with both 2 and 3 photon excitation and emission MP-STEM imaging. With 3 photon imaging, image depth approaching one millimeter can be achieved enabling in-vivo examination of tissue metabolism to a depth of up to 1 millimeter. A 4-photon excitation process for certain molecules move the excitation window far into the IR, where water absorption increases.

For depth in in-vivo MP-STEM imaging, the water windows at 1300 nm and 1650-1850 nm can be used. In these wavelength ranges images down to 1 mm and more can be obtained. As shown in the Table in FIG. 5, MP-STEM imaging with 3 or 4 photons, from the pump and probe beams can be used for the electron transport cofactors. The limit in IR wavelength is due to the increasing water absorption above about 1800 nm.

Figure 7:
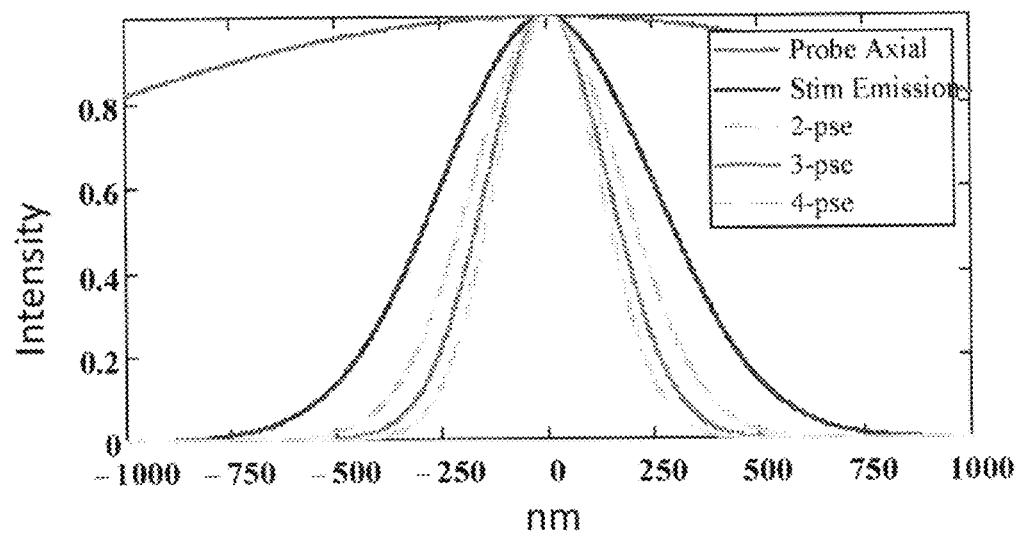
FIG. 7 is a plot of the x axial PSF for various MP-STEM systems for 1pse (2 photons), 2pse (4 photons), 3pse (6 photons) imaging and 4pse (4 photons) imaging.

FIG. 7 shows the axial (along the optic axis of the microscope) and FIG. 8 shows transverse (in the image plane of the detection microscope focus) $PSF_{st}$ of an OB-STEM system. The pump wavelength of 1080 nm and a probe wavelength of 1380 nm. The pump is a Bessel beam illumination system with an NA maximum 0.53 and minimum of 0.50. For the standard one photon pump and one photon probe STEM, a secondary annulus with a phase gradient is used to destructively interfere with secondary Bessel functional second maximum along the probe/detection optical axis. For the multiphoton excitation, the secondary Bessel lobes are reduced via multiphoton processes. In this system the probe/detection microscope system has a numerical aperture (NA) of 0.9.

Plotted in FIG. 7 are the axial ($PSF_{st}$)'s for the probe beam, a STEM system, a 2pse MP-STEM system, a 3pse MP-STEM system and a 4pse MP-STEM system. The PSF of the one photon STEM system is about 42% of the probe wavelength enabling some dipole-like backscatter imaging. The PSF of the 2pse system axial ½ width is about 31% of the probe wavelength enabling more dipole-like backscatter. The axial PSF of the 3pse system is about 25% of the probe wavelength. As shown in FIG. 9 single and multiple LS-STEM systems produce dipole backscatter.

Figure 8A:
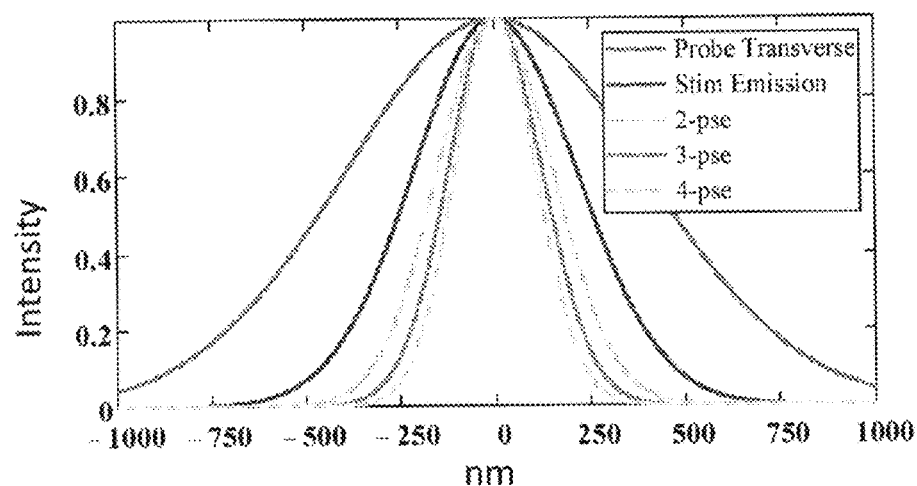
FIG. 8a is a plot of the transverse y axis PSF for 1pse (2 photons), 2pse (4 photons), 3pse (6 photons) imaging and 4pse (4 photons) imaging.
Figure 8B:
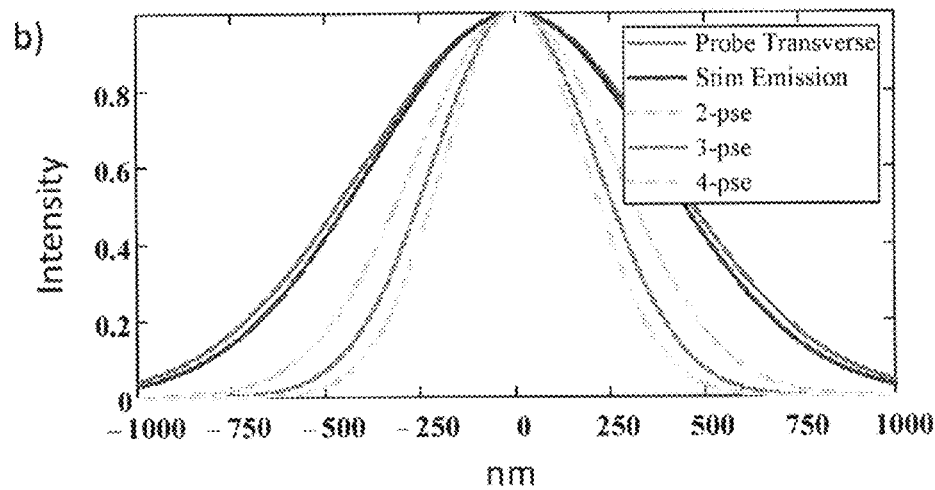
FIG. 8b is a plot of the transverse z axis PSF for 1pse (2 photons), 2pse (4 photons), 3pse (6 photons) imaging and 4pse (4 photons) imaging.

The transverse resolution shown in FIGS. 8a and 8b show that there are two different transverse resolutions in the LS-STEM system. In this case, a linear probe beam is used to stimulate emission. If structured illumination is used, the resolution along the z axis can be doubled. As shown in FIG. 8a where the resolution determined in part by the Bessel beam, while the resolution along the Bessel beam is determined primarily by the probe beam $PSF_{pr}$. The calculation of the resolution of the standard single photon LS-STEM system is an over estimate of the response because the secondary Bessel lobes contributions are ignored in this calculation. Transverse resolution can be increased a factor of about 2 by implementing structured illumination as shown in FIG. 2 and FIG. 11b.

In the implementations and methods disclosed here, the use of MP-STEM imaging can determine the molecular fluorescent lifetime by measuring the signal with two or more temporal delays between the pump and probe laser pulses. Two different time delay measurements can be used to measure the molecular concentrations with a single decay constant. This process is called stimulated emission Fluorescent Lifetime Microscopy (seFLIM).

Stimulated Fluorescent, MP-STEM and LS-STEM Theory

The absorption cross section, $\sigma_{abs}$, for optical radiation for a single chromophore at room temperature is about 10-16 cm2. In a tightly focused laser beam with a beam waist, S (~10–9 cm2) the integrated intensity attenuation of the excitation pump beam $\Delta I_{pu}/I_{pu}$ is proportional to the ratio between $\sigma_{abs}$ and S, where $I_{pu}$ is the intensity in the excitation pump beam as shown in Eq 1:

$$\Delta I_{pu}/I_{pu} = -N_0 \sigma_{abs}/S \qquad (1)$$

$N_0$ is the number of molecules in the ground state. For a single chromophore, $\Delta I_{pu}/I_{pu}$ is of the order of $10^{-7}$. The stimulated emission cross section, $\sigma_{stim}$, is comparable to the $\sigma_{abs}$, and the change in intensity of a stimulated probe beam $I_{pr}$ is:

$$\Delta I_{pr}/I_{pr} = -N2 \sigma_{stim}/S \qquad (2)$$

$N_2$ is the small number of molecules transiently probed by the stimulating probe beam. For a single chromophore $\Delta I_{pr}/I_{pr} = 10^{-7}$.

Normally, SEM is conducted in a non-saturating condition of the four-level system (FIG. 1a). Under this condition, N2 in equation (2) originates from a linear excitation: $N_2 \propto N_0 I_{pu} \sigma_{abs[0 \to 1]}/S$. This relation, together with equation (1), indicates that the final signal $\Delta I_{pr}$ is linearly dependent on both $I_{pu}$ and $I_{pr}$:

$$\Delta I_{pr} \propto N_0 I_{pu} I_{pr} (\sigma_{abs[0 \to 1]}/S)/(\sigma_{stim[2 \to 3]}/S) \qquad (3)$$

The MPE and MP-STEM each require two or more photons to interact simultaneously with the fluorescent molecules. However, in MP-STEM the two processes of excitation and stimulated emission can be separated in time by 0.3-4000 ps, and thus can initially be considered to be independent. The time scale of the "simultaneous" arrival of the photons is determined by the intermediate virtual lifetime $\Delta\tau \approx 10^{-16}$ s (as per the uncertainty principle). Hence, a 2-photon cross section ($\sigma_2$) is about $10^{-49}$ cm$^4$ (s/photon) (or $A^2\Delta\tau$), a 3-photon cross section ($\sigma_3$) is about $10^{-82}$ cm$^6$ (s/photon)$^2$ (or $A^3\Delta\tau^2$) and a 4-photon process is about $10^{-115}$ cm$^{10}$ (s/photon)$^3$ (or $A^4\Delta\tau^3$). These small cross sections require higher incident laser focal intensities, and shorter pulses in MP-STEM than single photon SEM. Pulses of less than 100 fs/pulse are often used. This is true for both the pump and probe beams.

Only one MP-STEM emission process/molecule/pulse can occur. Therefore the pump pulse can operate very close to saturation at focus of the transition to achieve the maximum population in the excited state, and to increase the probability of the stimulated emission pulse to de-excite pumped molecules. In saturation about 40-50% of the molecules at focus can be transferred to the excited state during the 100 fs excitation pulse, thus $N_2 \approx N_0/2$, and:

$$\Delta I_{pr} \propto N_0 I_{pr}/2(\sigma_{stim[2\rightarrow3]}/S) \quad (4)$$

An n-photon excitation or emission process is proportional to $\sigma_n I_{peak}^n \tau$, where $I_{pk}^n$ is the pump or probe peak intensity, $\sigma$n is the n photon cross section, and $\tau$ is the pulse length. For a square pulse in time at saturation: $\sigma n I_{peak}^n \tau = 1$. Therefore, the saturation peak intensity for the pump beam is:

$$I_{pks}^n \approx (\sigma_n \tau)^{-1/n} \quad (5)$$

The probe beam can operate at the high end of the linear gain curve to enable computation of molecular concentrations that require a linear relationship of the gain and the concentration. This occurs at about 50-60% of saturation.

Using diffraction limited focusing geometry, the relation between the average incident photon flux ($P_{avg}$, in units of photons/s) and $I_{peak}$ is:

$$P_{avg} \approx (0.61)^2 \lambda^2 (f \cdot \tau) I_{peak}/(NA)^2 \quad (6)$$

where f is the pulse repetition rate. Combing Eq. 6 and the saturation power for the n photo process ($P_{avg}^{ns}$) can be estimated as:

$$P_{avg}^{ns} \approx (0.61)^2 \lambda^2 (f \cdot \tau) \cdot (\sigma_n \tau)^{-\frac{1}{n}} / (NA^2) \quad (7)$$

The maximum intensity at focus in practice is limited by optical breakdown of the tissue and is wavelength dependent. The pulsed optical damage threshold measured for photon wavelengths above 1 μm for 100 fsec pulses has been shown to be about $2 \times 10^{14}$ W/cm$^2$, or about 20 nJ/μm$^2$/(100 fs pulse). Below 1 μm wavelength the damage threshold increases. With a high NA (1.3) objective lens, a Gaussian focal spot and 100-fs pulses at 80-MHz repetition rate and 1.0 um excitation wavelength, the estimated saturation powers for one, two, three, and four-photon processes are, respectively, ≈0.3 mW (0.1 nJ/pulse), ≈30 mW (1 nJ/pulse), ≈150 mW (5 nJ/pulse), and ≈300 mW (10 nJ/pulse) by Eq. 8 and the excitation cross sections estimated above. Thus in the limit the damage threshold for 2pse and 3spse is more limited by average power of the pump and probe beams than the damage threshold for 70-100 fs NIR pulses. However for the lower NA objectives used in LS-STEM the energy/pulse and the average energy of the laser can be increased to enable maximum back scattered signal. The required saturation power scales as 1/NA$^2$ as shown in equations 6 and 7. Therefore, the Gaussian probe beam power can be increased by about 1.8 times in going from a 1.2 to a 0.9 Gaussian beam. In the Bessel probe beam, the narrowness of the central lobe compensates for the lower NA used. However, how the laser energy is distributed to the annular illumination zone has an effect on the laser power required.

The laser power used will have to be increased for imaging at 1-3 absorption/scattering depths. At 800 nm, the absorption depth in tissue is 120 μm, at 1000 nm wavelength the absorption depth in brain tissue is ~200 μm, and at 1300 nm the absorption depth is 300 μm. Therefore it is advantaged to operate above 1 micron in pump wavelength. MP-STEM can operate at about 0-3 absorption depths (15% transmission to focus for the pump wavelength). Thus the maximum incident estimated laser power for two and three-photon processes are, respectively, ≈600 mW (20 nJ/pulse) and ≈3000 mW (100 nJ/pulse) at the surface. These average powers are high. It is sometimes better to operate at a reduced laser rep rate of 10 MHz. Reducing the laser repetition rate can have an effect on the lock-in photon detection protocols. However, with the lower backscatter noise, and use of a differential detection imager, the use of low repetition rate laser systems can be used.

The Point Spread Function of a MP-STEM system (PSFMP-STEM) scales as the single photon illumination Point Spread Function (PSF$_{il}$) to the power equal to the number of photons in the process. The pump PSF (PSF$_{pu}$) and probe PSF (PSF$_{pr}$) are each raised to the power of the number of photons used per each electronic transition, n, and are multiplied together to produce the PSFMP-STEM as shown in eq (8).

$$((PSF_{MP-STEM}) = (PSF_{pu})^n \cdot (PSF_{pr})^n \quad (8)$$

FIGS. 7 and 8 a-b show the PSFs in both the axial and transverse direction for the probe beam, the standard STEM probe stimulated emission spot as well as the 2pse, 3pse and 4pse MP-STEM stimulated emission spots, for a 0.9 NA probe objective, and objective wavelength of 1380 nm. The pump beam uses a 0.53 outer annulus and 0.50 inner annulus and a probe wavelength of 1020 nm. These wavelengths are useful for 3pse from NADH and are used throughout the examples given below.

It is known that a single fluorophore will emit stimulated emission into the backward illumination and forward propagating modes into the stimulating mode with equal probability. The fluorophore is small relative to the optical wavelength and cannot tell the direction of propagation of the field. However, as the stimulated emission gain length increases the backscatter decreases. Although the gain in the stimulated field is small in microscopy because of the small focal spot, as the probe beam propagates along the forward direction through the focal spot the stimulated emission photons add in phase, increasing the coherent traveling field. The stimulated emission in the back propagation direction adds out of phase as the incident beam propagates forward. Thus as the gain medium length increases, the back scattered stimulated emission photons from axially spatially separate fluorophores destructively interfere. The backscatter stimulated field quickly decreases over sub-wavelength dimensions. This small sample coherent backscatter is related to the small structure backscatter in Coherent Anti-Stocks Raman Scattering.

The forward and back scattered fields generated along the optic axis can be modeled over the focal spot of length 2Z1 by the following equation:

$$G_{(f,b)}(t) = \int_{-z1}^{z1} C(z) E_{pr} Re\{e^{-i(kx+w_{pr}t+\theta(z))}\} PSF_{axial}(z) dz \quad (9)$$

$G_f$ is the forward far field electric field gain, and $G_b$ backward far field electric field gain. $E_{pr}$ is the probe electric field, $\omega_{pr}$ is the probe frequency, k is the propagation constant and $\theta(z)$ is the phase of the emitted photons at each point. C(z) is the gain factor that depends on the local concentration of fluorophores and stimulated emission cross section. It is assumed that in the forward direction $\theta(z)=0$ for all points, as the stimulated photons add in phase. In the backward propagating direction $\theta(z)$ is different at each point as the there is a time change for the emission of each axial point. It assumes that z=0 is at the center of the $PSF_{axial}(z)$, and at that point $\theta(z)=0$.

FIG. 9 plots the ratio of the forward to back scattered electric field gain ($G_f/G_b$) for a Gaussian distribution of excited states along the optic axis as a function of the ratio of stimulating wavelength $\lambda_{pr}$ to Gaussian ½ width, w, that is ($\lambda_{pr}/w$). For $\lambda_{pr}/w>8$ the backscatter gain approaches the forward gain, while for $\lambda_{pr}/w<1.5$ the backscatter approaches zero. The total Gain is thus $G_f+G_b$, when $\lambda_{pr}/w>8$, $G_f=G_b$.

For a uniform volume of emitters the optimum signal is achieved for a $\lambda_{pr}/w \approx 4$-5. For larger $\lambda_{pr}/w$ ratios, the emission spot is small and the number of emitters present produces weak stimulated emission. The PSF of the one photon STEM system achieves a $\lambda_{pr}/w \approx 2.4$. This will result in backscatter equal to about 15% the forward scatter enabling some dipole-like backscatter imaging. The axial $PSF_{st}$ of the 2pse system achieves $\lambda_{pr}/w \approx 3.2$. The axial $PSF_{st}$ of the 3pse system achieves $\lambda_{pr}/w\beta 4.0$. Thus the LS-STEM results in measureable dipole backscatter for STEM and MP-STEM illumination and detection strategies.

In a confocal microscope, backscatter dipole emission from a focal spot with less than ½ wavelength axial dimension, while the background noise comprises back scattered probe photons from refractive index (RI) gradients in the focal volume and multiple back scattered photons back that make it into the confocal aperture. RI noise is at most about $5 \times 10^{-4}$ of the incident beam, at the interface of cytoplasm and cell nuclei. Thus backscatter noise is less than forward scatter noise. The signals and sources of forward and back scattered signals and noise are summarized in FIG. 10.

Dipole-like scattering is particularly important in deep tissue imaging. This enables much more signal light and fewer background photons to be collected in the illumination aperture of the microscope. In addition it provides a confocal scattering image of the tissue understudy, enabling at least two forms of imaging with each image scan-scattered photon imaging and stimulated emission imaging. These two imaging modes can coherently interfere with each other.

One can calculate the sensitivity, and the required pixel dwell time for a high speed MP-STEM and LS-STEM system. The largest signals are achieved for pumping at saturation, and stimulated emission probe at near 60% of saturation. At pump saturation 50% of the molecules at focus will be in the lowest excited state after decay from the upper pumped level. With 100 fs pump pulses we assume no decay out of the pumped levels during the pulse. The maximum photo-pumped population is 50% given the equivalence of the Einstein emission and absorption coefficients. However in the probe beam, it is desirable to provide stimulated emission gain that is in the linear range to provide an accurate measure of the concentration of emitters.

Again because the probe pulse is about 100 fs there is minimal decay from the upper and lower excited states during the probe pulse and about 50% of the molecules will be in each the upper and lower level of the transition. Thus the probe intensity can be below the stimulated emission saturation intensity, e.g., the probe beam intensity can be about 60% of fluorescent saturation, in order to maintain linearity of probe gain.

LS-STEM can provide close to real time imaging. We can collect light from 250 linear channels simultaneously. For a 500×500 pixel image, 1000 pixel dwell times are preferred. One half of the dwell time is acquired with the pump on, and one half of the dwell time is acquired with the pump off. For a 0.5 second image time, a total pixel dwell time of 500 microseconds is used.

For a 3spe system designed to detect NADH at a 20 MHz laser pulse repetition rate, and a 2 MHz sample window (~10 pulses/sample window) in the ≈100 mW (2.0 nJ/pulse) 1020 nm pump region and ≈120 mW (1.2 nJ/pulse, 8.6×10⁹ photons/pulse) 1380 nm probe region. The power at the surface varies from the focal power numbers to about 10 times higher depending on the focal depth.

The pump power is in saturation and the probe power is at the high end of the linear gain region. For the probe at 20 MHz laser repetition rate about $8.6 \times 10^{13}$ photons in 10,000 pulses are delivered per pixel/(500 µs dwell time). Half of the probe pulses are delivered with the pump pulse off. In the 5,000 pulses with both probe and pump on, each molecule can be excited at most 5,000 times (once per pulse) if the pump power drives molecular transitions into saturation. In addition, in the limit 2,500 stimulated emissions are back scattered for a small volume of emitters. The maximum back scattered noise (such as at the cell nucleus interface) is about $2.1 \times 10^9$, thus the back scattered noise/pixel dwell time with the pump on (or off) per pixel is about $4.6 \times 10^4$ photons. The signal is in the linear part of the probe gain curve, and thus about 2,500×n gain photons/molecule can be added to the probe gain/pixel dwell time. Thus in the limit in a high noise pixel, when n=3 about 6 molecules signal equal to RI gradient noise. Thus a dynamic range of $10^5$ achieved with a lock-in amplifier array system can detect 10 molecules/pixel. If 2000 molecules contribute to the back scattered signal then a standard imager with a dynamic range of 1000 would be adequate.

For the system parameters in FIG. 9, the ½ width of the focal ellipsoid is ~0.03 µm³, and the required emitter concentration for high SNR rapid scanning is below the mM range. This is less than to the concentration of NADH in cells. In mitochondria, the concentration of NADH is higher.

In stimulated coherent spectroscopy, the detected signal can be described in terms of classical wave interference in the far field. The induced signal field $E_s$ of frequency $\omega_s$, is generated at point r through a nonlinear process and is detected at a far-field point R. At the detection point, the induced field is mixed with a local oscillator field $E_{LO}(R)$, which is phase coherent with the former. The total intensity at the far field detector is then written as:

$$S(R) = \left(\frac{n(\omega_s)c}{8\pi}\right)|E_s(R) + E_{LO}(R)|^2 = I_s(R) + I_{LO}(R) + \frac{2n(\omega_s)c}{8\pi} Re\{E_s(R) \cdot E_{LO}^*(R)\}$$

where $n(\omega_s)$ is the refractive index of the material at frequency $\omega_s$, c is the speed of light, and $I_s$, $I_{LO}$ are the intensities of the induced signal and the local oscillator fields, respectively The fields E(R) are complex with a given wave vector that depends parametrically on R. The heterodyne contribution to the signal through which stimulated coherent optical signals can be understood is shown in Eq. (10)

$$S_{het}(R) = \frac{2n(\omega_s)c}{8\pi} \text{Re}\{E_s(R) \cdot E^*_{LO}(R)\} \tag{10}$$

The excitation field provides the local oscillator that interferes with the signal field in the far field.

Coherent stimulated multiphoton processes can be analyzed in terms of the third, or higher, order molecular susceptibility. MP-STEM is different from SRS because the pump beam does not coherently participate in the multiphoton stimulated emission process. The Kasha decay from the pumped excited band into the lowest excited state and the variable delay between the pump and probe pulses causes a loss of coherence between excitation and stimulated emission processes. However, the pump does contribute to the process by creating the population of excited states that participate in stimulated emission.

In forward scattered MP-STEM the signal of interest is the probe gain field $G_{pr}(r)$ or the signal field $E_{si}(r)$, which depends upon the induced polarization, $P_{pr}^n(\omega_{pr},r)$, generated at focus, where n is the number of emitted probe photons per event, and is described by Eq. 11, $$P_{pr}^n(\omega_{pr},r) \propto |E_{pr}(r)|^{2n-2} \cdot E_{pr}(r) \cdot I_{pu}^n(r) \cdot e^{-\Delta t/\tau} \cdot \chi^{2n-1}(\omega_{pr},r) \tag{11}$$

Here $\chi^{2n-1}(\omega pr,r)$ is the molecular susceptibility of the medium for the relevant order of susceptibility. $E_{pr}$ is the probe electric field, $I_{pu}$ is the pump intensity, and $\Delta t$ is the delay between the peak of the pump pulse and the peak of the probe pulse, $\tau$ is the excited state decay constant.

In 2 photon excitation and stimulated emission processes a third order susceptibility is used, while in 3 photon excitation and stimulated processes a fifth order susceptibility is require.

The induced electric field $E_{si}$ generated at point r near focus is detected at a far field point R where it is mixed with a local oscillator field that is phase coherent with the induced field. In the forward direction the local oscillator field is $E_{pr}$, while in the backscatter direction the local oscillator field is the index gradient backscatter field $E_{bs}$ as shown in FIG. 10. A spatial phase shift for the measured field at a detection point R relative to the phase at the excitation point r can occur, which depends on the excitation and detection geometry. For forward scatter it is assumed that $\varphi$ is the spatial phase of the induced field at R relative to the phase at the origination point r, and a measures a similar spatial phase shift between r and R for the probe local oscillator field. These relations are shown in Eq. 12 and Eq. 13

$$E_s(R) \approx P_n(\omega_{pr},r)e^{-i\phi} \tag{12}$$

$$E_{LO}(R) \approx E_{pr}(r)e^{-i\alpha} \tag{13}$$

The stimulated field in a MP-STEM microscope be using eq. 12 and eq. 13;

$$E_s(R) = \tag{14}$$
$$P_{pr}^n(\omega_{pr},r) \propto |E_{pr}(r)|^{2(n-1)} \cdot E_{pr}(r) \cdot I_{pu}^n(r) \cdot e^{-\frac{\Delta t}{\tau}} \cdot \chi^{2n-1}(\omega_{pr},r) \cdot e^{-i\Phi}$$

When the stimulated emission from a plane of dipoles perpendicular to the direction of field propagation, is measured in the far field, there is $\phi=-\pi/2$ radian change in the phase between the dipole emission plane and the far field. When a single dipole is present at focus, the induced field exhibits a phase that is spatially invariant, i.e., $\phi=0$.

In a MP-STEM microscope the scattering volume can be treated as a dipole, as it is less than a wavelength in the transverse dimensions. Therefore in the far field, $\phi=0$. Thus the heterodyne term in the forward far field for a dipole at focus is shown in Eq. 15

$$S_{pr}^n(\omega_{pr},R) \propto [I_{pu}(r)]^n \cdot e^{-\Delta t/\tau} \cdot |E_{pr}(r)|^{2(n-1)} Re$$
$$\{\cdot E_{pr}(r) \cdot E^*_{pr}(R) \cdot \chi^{2n-1}(\omega_{pr},r)\} \tag{15}$$

This relation contains the term $E_{pr}(r) \cdot E^*_{pr}(R)$ which carries phase information that depends solely on the spatial profile of the excitation field. Using Eq. 13, this latter term can be rewritten as $|E_{pr}(r)|^2 e^{i\alpha}$. The Gouy phase shift in a high NA microscope system from the focus to the far field is $\alpha=\pi/2$. We can thus write:

$$S_{pr}^n(\omega_{pr},R) \propto [I_{pr}(r)]^n \cdot [I_{pu}(r)]^n \cdot e^{-\frac{\Delta t}{\tau}} \cdot \text{Im}\{\chi^{2n-1}(\omega_{pr},r)\} \tag{16}$$

Eq. (16) describes the forward scattered gain in MP-STEM heterodyne signal with the small scattered volume centered on the focal plane.

In MP-STEM backscatter signal detection, the local oscillator signal, when it is present, comes from probe beam reflection from refractive index field gradients and nanoparticles within the probe beam focus. The backscatter source can be anywhere within the single photon focus of the microscope, or the acceptance confocal pinhole aperture. Therefore, the effect of the Guoy phase, and focal position of the backscatter source and its interference with the MP-STEM signal can be considered. In deriving the backscatter field phase relative to the stimulated emission field we will follow the approach of Hwang and Moerner for nanoparticle scattering.

A nanoparticle can be modeled has having a real and imaginary scattering amplitude $\sigma/A+i\varphi$ where $\alpha/a$ is the real part responsible for absorption and $\varphi$ is the phase change associated with the transmission of a laser beam. After the nanoparticle, the probe field (with $e^{-i\omega t}$ assumed) is $$E_r(r) = E_{pr}(r) + E_{sc}(r) = E_{pr}(e^{ikr}) + \left(\frac{\sigma}{A}\right)E_{pr}(e^{ikr}) + i\varphi E_{pr}(e^{ikr}) \tag{17}$$

In the back scattered direction, the phase and refractive index gradient dependent scatter $E_{bsRI}(r)$ is of significance. Incorporating the phase of the induced backscatter, $\varphi_{sc}(z)$, $E_{bsRI}(r)$ is:

$$E_{bsRI}(r) \propto i\varphi E_{pr}(ikr+i\varphi_{sc}(r)) \tag{18}$$

This field interferes with the stimulated backscatter $E_{bsSE}$ (r). In order to calculate the far field signal, the contributions of the Gouy phase and the scatterer induced phase can be taken into account.

The Gouy phase shift of a 2 dimensional wavefront in a high NA microscope is a total of $\pi$ radians. The phase of the probe beam is described in FIG. 11. Near focus, at the distance z (z is positive for an advance in the propagation direction) on axis, the phase shift is given by $-\tan^{-1}(z/z_R)$, where $\omega_0$ is the beam radius at the focus (waist). The quantity $z_R$ is equal to $\pi\omega_0/\lambda_{pr}$, the Rayleigh range of the waist. This phase shift approaches a constant value of $\pi/2$ between the focal position and a large distance in the far field.

A forward scattered beam from a nanoparticle has a phase shift of $\pi/2$ radians both in the far-field and the near-field. That is, when a field is present at the input of a sub-wavelength aperture the phase change through the aperture is $\pi/2$. Using Babinet's principle, when the complimentary point scatterer (absorber, or refractive index gradient) is present, in place of the aperture, the scattered beam undergoes a phase change of $+\pi/2$ radians. Thus in the far field $\varphi(R)$ is:

$$\varphi(R) = \pi - \tan^{-1}\left(\frac{r}{r_R}\right) \quad (19)$$

The far field in the backscatter direction $E_{bs}$ is the sum of the backscatter refractive index gradient phase change particle scatter, $E_{bsRI}$, and the back scattered stimulated emission $E_{bsSE}$.

$$E_{bs}(R) = E_{bsRI}(R) + E_{bsSE}(R) \quad (20)$$

The back scattered intensity is $$I_{bs}(R) \propto I_{bsRI}(R) + I_{bsSE}(R) + Re\{E_{bsSE}(R) \cdot E^*_{bsRI}(R)\} \quad (21)$$

The dipole induced backscatter is assumed to originate from the plane of focus, while the index gradient backscatter can originate anyplace near focus. Therefore the contribution of a variable Gouy phase is mostly contributed by the RI induced scatter. Secondly in the backscatter direction the stimulated emission experiences a 0 phase shift as it propagates in the backward direction. We also assume since the n photon process is phase matched and resonant, such that the $re\{\chi^{2n-1}(\omega_{pr},r)\}=0$. Therefore using Eq 20 and Eq. 21 the heterodyne backscatter term $S_{bs}(R)$ is:

$$S_{bsv}(R) \propto \left[[I_{pr}(r)]^{n-1} \cdot [I_{pu}(r)]^n \cdot I_{bsRI}^{\frac{1}{2}}(r) \cdot I_{bsRI}^{\frac{1}{2}}(r) \cdot e^{-\frac{\Delta t}{\tau}} \cdot \text{Im}\right.$$
$$\left.\{\chi^{2n-1}(\omega_{pr}, r)\}\right]\left[1 - 2\varphi \sin\left(\tan^{-1}\left(\frac{z}{z_R}\right)\right)\right] \quad (22)$$

The backscatter from each pixel can have refractive index backscatter, stimulated emission backscatter or both. During the pulse train the presence or absence of back scatter can be determined by measuring the backscatter signal from pulses when the pump pulse is off. The position with the focus can be determined by interference of the backscatter with the pump off with a reference beam that can be used to focus the system. Many such approaches exist.

MP-STEM Signal Sensitivity and SNR

Large MP-STEM probe gain signals can be achieved when pumping at saturation. With 100 fs pump pulses, it is assumed there is no decay out of the excited state manifold in first 500 fs after the pulse. The maximum signals, for all fluorescent lifetimes, are achieved with a probe delay, $\Delta\tau_{pr}$, of about 0.5-1.0 ps.

The maximum photo-pumped population is 50% of the molecules at focus given the equivalence of the Einstein emission and absorption coefficients. It is desirable to provide stimulated emission gain that is in the linear range to provide an accurate measure of the concentration of emitters. Therefore, the probe beam intensity cannot produce saturation, but about 50% of fluorescent saturation.

The requirement for high spatial resolution for diffuse scatterers is unlikely unless there is a specific boundary near the resolution limit of the scan, such as in mitochondria. For concentrations of bound scatterers, the local concentration can be elevated. In cases like imaging RNA in ribosomes, many emitters can be present in a very small volume.

The concentration of NADH in cells is on average about 0.3 mM. The free to bound ratio of [NADH] ranges from 1-4. Bound molecules in mitochondria can have concentrations that are higher than average and thus can yield acceptable signals. To achieve acceptable signals of diffuse distribution of free NADH can require averaging over about 25 pixels or a cube about 5 pixels on a side or a length or about >2μ diameter if they are laid out on a square grid separated by the ½ width of the PSF.

Stimulated Raman Scattering LS-STEM

The energetics of SRSM is shown in FIG. 11. SRS differs from stimulated fluorescence in that the excited state is a virtual level, with a sub-femtosecond lifetime. Therefore, the pump and probe are delivered simultaneously to the focal region. SRS is a fully coherent process as compared to stimulated fluorescence which is a partially incoherent and partially coherent process. In order to perform the coherent SRS process the pump and probe beams can have the same polarization direction. This is accomplished if the pump and probe beams are linearly polarized along the x axis, which is the one axis transverse to both beamlines.

Orthogonal Beam SRSM (OB-SRSM) uses single photons for excitation and one for stimulated emission. OB-SRSM uses the same setup as stimulated fluorescence shown in FIG. 2.

OB-SRSM systems may remove the secondary Bessel beam peaks along the y-axis, in order to remove the secondary lobes of the pump beam along the probe axial dimension better localization of stimulated dipole backscattering. Multiphoton excitation to reduce secondary lobes is not appropriate for axial focal spot reduction in OB-SRSM. Removal of the secondary peaks is accomplished by the use of a second annulus, with an annular phase gradient that causes destructive interference of the secondary peaks in the excitation illumination profile as shown by Zhang et al. FIG. 13a shows the dual annular structure. This figure is taken from Zhang et al. The parameters used to create the zero-order Bessel beam are maximum 0.53 Bessel NA=and minimum Bessel NA=0.516, and those used to create the second-order Bessel beam in the second annulus are max NA=0.516 and min NA=0.5. As shown, in FIG. 13c destructive coherent superposition of the two beams at azimuthal angles $\varphi=0$ and $\varphi=\pi$ leads to reduced side-bands along the y-axis, but enhancement of secondary lobes in the x direction at $\varphi=\pm\pi/2$. However, if a detection objective (e.g. a CFI APO 40x/0.8 NA water-dipping objective with a working distance of 3.5 mm, Nikon) is aligned with its optical axis along y with the stimulated emission detected at 90° from the axis of the excitation beam, as shown in FIG. 2, the contribution of stimulated emission emitted from the sidebands at $\varphi=\pm\pi/2$ can be mitigated by confocal detection. In particular, using a slit as a spatial filter in confocal detection spatially filters both in the direction perpendicular to the slit as well as axially. The axial rejection, however, is a weak function of z, whereas the perpendicular spatial filtering is a strong function of distance. Here, the destructively interfered regions of the excitation beams are aligned along the optical axis of the collection objective, minimizing the need for spatial filtering in this direction. Using structured illumination for the probe beam further enhances the filtering if an array of pinholes is used in the detection beamline as shown in FIG. 2.

It should be noted that the use of the secondary annulus in the pump beam is not required to enable dipole back scatter. Calculations show that a good backscatter signal is still present even with the secondary lobes.

The use of high speed Raman detection can be used for 3-Dimensional image reconstruction in pathology using CH2 and CH3 vibrational signals to look at nucleic acid and protein signals. Single photon STEM or MP-STEM can be used for 3-Dimensional reconstruction in melanoma or with protein and nucleic acid stimulated fluorescence. Resolution can be varied by using variable pump/detection objectives. This enables imaging Raman signals from lower concentrations of molecules, faster scans more rapid 3-d reconstruction.

The foregoing Detailed Description is to be understood as being in every respect illustrative, but not restrictive, and the scope of the disclosed technology disclosed herein is not to be determined from the Detailed Description, but rather from the claims as interpreted according to the full breadth permitted by the patent laws. It is to be understood that the implementations shown and described herein are only illustrative of the principles of the disclosed technology and that various modifications can be implemented without departing from the scope and spirit of the disclosed technology.

The invention claimed is:

1. A microscopy system comprising:
   a first laser emitting a first laser pulse along a first beam line, the first laser pulse being converted into an annular Bessel pump beam; and
   a second laser emitting a second laser pulse along a second beam line, the second laser pulse being a probe beam, the annular Bessel pump beam and the probe beam arriving at a sample at right angles to each other thereby allowing the annular Bessel pump beam to shrink a focal axial diameter of the second beam line and enabling dipole-like backscatter stimulated emission along the second beam line.

2. The microscopy system of claim 1 wherein the annular Bessel pump beam is composed of multiple points of illumination around the annular Bessel pump beam producing an optical light sheet being delivered to the sample.

3. The microscopy system of claim 2 wherein the optical light sheet is focused to one of a line or a series of dots.

4. The microscopy system of claim 1 wherein the second beamline collects the dipole-like back scattered stimulated emission and focuses the dipole-like back scattered stimulated emission on a confocal aperture array.

5. The microscopy system of claim 1 further comprising: at least one time delay component along the second beam line for delaying the probe beam, the at least one time delay component delaying the probe beam by 0.3 ps to 5 ns relative to the pump beam.

6. The microscopy system of claim 1 wherein the probe beam is one of a single confocal, a Bessel beam spot, a continuous linear illumination, a one-dimensional array of spots or two-dimensional array of spots.

7. The microscopy system of claim 1 further comprising: a galvanometer scanning system along the first beam line that scans the annular Bessel pump beam to fill in a two dimensional image in a detector located along the second beam line.

8. The microscopy system of claim 1 further comprising: a galvanometer scanning system along the second beam line that scans the probe beam to fill in focal spots of the annular Bessel pump beam.

9. The microscopy system of claim 1 wherein the microscopy system enables reduction of an axial dimension of a stimulated emission focal spot to less than 50% of a wavelength of a stimulated emission photon.

10. The microscopy system of claim 1 further comprising: an acousto-optic modulator for modulating the annular Bessel pump beam on and off.

11. A microscopy method comprising the steps of:
    emitting a first laser pulse along a first beam line;
    converting the first laser pulse into an annular Bessel pump beam;
    emitting a second laser pulse along a second beam line, the second laser pulse being a probe beam; and
    delivering the annular Bessel pump beam and the probe beam to a sample so that the annular Bessel pump beam and the probe beam arrive at the sample at right angles to each other thereby allowing the annular Bessel pump beam to shrink a focal axial diameter of the second beam line thus enabling dipole-like backscatter stimulated emission along the second beam line.

12. The microscopy method of claim 11 wherein the pump beam is composed of multiple points of illumination around the annular Bessel pump beam producing an optical light sheet being delivered to the sample.

13. The microscopy method of claim 12 wherein the optical light sheet is focused to one of a line or a series of dots.

14. The microscopy method of claim 11 wherein the second beamline collects the dipole-like back scattered stimulated emission and focuses the dipole-like back scattered stimulated emission on a confocal aperture array.

15. The microscopy method of claim 11 further comprising the steps of: delaying the probe beam by 0.3 ps to 5 ns relative to the pump beam.

16. The microscopy method of claim 11 wherein the probe beam is one of a single confocal, a Bessel beam spot, a continuous linear illumination, a one-dimensional array of spots or two-dimensional array of spots.

17. The microscopy method of claim 11 further comprising the steps of: scanning the annular Bessel pump beam along the first beam line to fill in a two dimensional image in a detector located along the second beam line.

18. The microscopy method of claim 11 further comprising the steps of: scanning the probe beam along the second beam line to fill in focal spots of the annular Bessel pump beam.

19. The microscopy method of claim 11 wherein the microscopy system enables reduction of an axial dimension of a stimulated emission focal spot to less than 50% of a wavelength of a stimulated emission photon.

20. The microscopy method of claim 11 further comprising the steps of: modulating the annular Bessel pump beam on and off.

* * * * *